(12) United States Patent
Ben-David et al.

(10) Patent No.: US 8,565,896 B2
(45) Date of Patent: Oct. 22, 2013

(54) ELECTRODE CUFF WITH RECESSES

(75) Inventors: Tamir Ben-David, Tel Aviv (IL); Ehud Cohen, Ganei Tikva (IL); Noam Gavish, Hod Hasharon (IL); Shai Ayal, Shoham (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 204 days.

(21) Appl. No.: 12/952,058

(22) Filed: Nov. 22, 2010

(65) Prior Publication Data

US 2012/0130463 A1    May 24, 2012

(51) Int. Cl.
  *A61N 1/05*  (2006.01)
(52) U.S. Cl.
  USPC .......................................................... 607/117
(58) Field of Classification Search
  USPC .......................................................... 607/118
  See application file for complete search history.

(56) References Cited

U.S. PATENT DOCUMENTS

| | | | |
|---|---|---|---|
| 4,010,755 A | 3/1977 | Preston | |
| 4,026,300 A | 5/1977 | DeLuca et al. | |
| 4,161,952 A | 7/1979 | Kinney et al. | |
| 4,535,785 A | 8/1985 | Van den Honert | |
| 4,573,481 A | 3/1986 | Bullara | |
| 4,602,624 A | 7/1986 | Naples et al. | |
| 4,608,985 A | 9/1986 | Crish et al. | |
| 4,628,942 A | 12/1986 | Sweeney et al. | |
| 4,649,936 A | 3/1987 | Ungar et al. | |
| 5,095,905 A * | 3/1992 | Klepinski | 600/377 |
| 5,143,067 A * | 9/1992 | Rise et al. | 600/377 |
| 5,170,802 A | 12/1992 | Mehra | |
| 5,199,430 A | 4/1993 | Fang et al. | |
| 5,203,326 A | 4/1993 | Collins | |
| 5,224,491 A | 7/1993 | Mehra | |
| 5,243,980 A | 9/1993 | Mehra | |
| 5,282,468 A | 2/1994 | Klepinski | |

(Continued)

FOREIGN PATENT DOCUMENTS

| | | |
|---|---|---|
| DE | 198 47 446 | 4/2000 |
| EP | 0 688 577 | 12/1995 |

(Continued)

OTHER PUBLICATIONS

An Office Action dated Dec. 2, 2011, which issued during the prosecution of U.S. Appl. No. 12/012,366.

(Continued)

*Primary Examiner* — Niketa Patel
*Assistant Examiner* — Christopher A Flory
(74) *Attorney, Agent, or Firm* — Sughrue Mion, PLLC

(57) ABSTRACT

An electrode assembly includes one or more electrode contact surfaces, and a cuff, to which the contact surfaces are fixed, and which comprises an electrically insulating material, is configured to assume open and closed positions, and, when in the closed position, is shaped so as to define a plurality of planar cross sections perpendicular to a longitudinal axis of the cuff, distributed continuously along an entire length of the cuff along the longitudinal axis, such that the perpendicular cross sections define respective inner closed curves that together define an inner surface that defines and completely surrounds a volume that extends along the entire length of the cuff. The inner closed curves of at least two of the perpendicular cross sections would cross, and not merely intersect, one another if superimposed while preserving orientation and position of the perpendicular cross sections with respect to the cuff. Other embodiments are also described.

27 Claims, 11 Drawing Sheets

(56) References Cited

U.S. PATENT DOCUMENTS

| | | |
|---|---|---|
| 5,334,221 A | 8/1994 | Bardy |
| 5,344,438 A * | 9/1994 | Testerman et al. ............ 607/118 |
| 5,356,425 A | 10/1994 | Bardy et al. |
| 5,400,784 A | 3/1995 | Durand et al. |
| 5,411,531 A | 5/1995 | Hill et al. |
| 5,423,872 A | 6/1995 | Cigaina |
| 5,487,756 A | 1/1996 | Kallesoe et al. |
| 5,507,784 A | 4/1996 | Hill et al. |
| 5,628,777 A | 5/1997 | Moberg et al. |
| 5,634,462 A | 6/1997 | Tyler et al. |
| 5,690,681 A | 11/1997 | Geddes et al. |
| 5,700,282 A | 12/1997 | Zabara |
| 5,755,750 A | 5/1998 | Petruska et al. |
| 5,800,470 A | 9/1998 | Stein et al. |
| 5,824,027 A | 10/1998 | Hoffer et al. |
| 5,833,664 A | 11/1998 | Seare, Jr. |
| 5,893,881 A | 4/1999 | Elsberry et al. |
| 5,916,239 A | 6/1999 | Geddes et al. |
| 5,919,220 A | 7/1999 | Stieglitz et al. |
| 5,938,596 A | 8/1999 | Woloszko et al. |
| 6,006,134 A | 12/1999 | Hill et al. |
| 6,038,477 A | 3/2000 | Kayyali |
| 6,058,331 A | 5/2000 | King et al. |
| 6,073,048 A | 6/2000 | Kieval et al. |
| H1905 H | 10/2000 | Hill |
| 6,161,029 A | 12/2000 | Spreigl et al. |
| 6,178,349 B1 * | 1/2001 | Kieval ................ 607/3 |
| 6,230,061 B1 | 5/2001 | Hartung |
| 6,292,695 B1 | 9/2001 | Webster, Jr. et al. |
| 6,292,703 B1 | 9/2001 | Meier et al. |
| 6,298,268 B1 | 10/2001 | Ben-Haim et al. |
| 6,308,105 B1 * | 10/2001 | Duysens et al. ............ 607/118 |
| 6,317,631 B1 | 11/2001 | Ben-Haim et al. |
| 6,341,236 B1 | 1/2002 | Osorio et al. |
| 6,363,279 B1 | 3/2002 | Ben-Haim et al. |
| 6,445,953 B1 | 9/2002 | Bulkes et al. |
| 6,456,866 B1 | 9/2002 | Tyler et al. |
| 6,463,324 B1 | 10/2002 | Ben-Haim et al. |
| 6,542,774 B2 | 4/2003 | Hill et al. |
| 6,564,096 B2 | 5/2003 | Mest |
| 6,600,954 B2 | 7/2003 | Cohen et al. |
| 6,600,956 B2 | 7/2003 | Maschino et al. |
| 6,611,713 B2 | 8/2003 | Schaurete |
| 6,628,987 B1 | 9/2003 | Hill et al. |
| 6,684,105 B2 | 1/2004 | Cohen et al. |
| 6,712,772 B2 | 3/2004 | Cohen et al. |
| 6,839,594 B2 | 1/2005 | Cohen et al. |
| RE38,705 E | 2/2005 | Hill et al. |
| 6,850,801 B2 | 2/2005 | Kieval et al. |
| 6,865,416 B2 | 3/2005 | Dev et al. |
| 6,866,657 B2 * | 3/2005 | Shchervinsky ............ 604/266 |
| 6,892,098 B2 | 5/2005 | Ayal et al. |
| 6,907,295 B2 | 6/2005 | Gross et al. |
| 6,934,583 B2 | 8/2005 | Weinberg et al. |
| 6,937,897 B2 | 8/2005 | Min et al. |
| 6,985,774 B2 | 1/2006 | Kieval et al. |
| 7,020,530 B1 | 3/2006 | Ideker et al. |
| 7,027,876 B2 | 4/2006 | Casavant et al. |
| 7,087,053 B2 | 8/2006 | Vanney |
| 7,113,816 B2 * | 9/2006 | Matsukawa et al. .......... 600/377 |
| 7,123,961 B1 | 10/2006 | Kroll et al. |
| 7,139,607 B1 | 11/2006 | Shelchuk |
| 7,167,748 B2 | 1/2007 | Ben-Haim et al. |
| 7,212,870 B1 | 5/2007 | Helland |
| 7,218,971 B2 | 5/2007 | Heil et al. |
| 7,225,016 B1 * | 5/2007 | Koh ................ 607/2 |
| 7,236,821 B2 | 6/2007 | Cates et al. |
| 7,245,967 B1 | 7/2007 | Shelchuk |
| 7,248,930 B1 * | 7/2007 | Woloszko et al. ............ 607/118 |
| 7,269,457 B2 | 9/2007 | Shafer et al. |
| 7,295,881 B2 | 11/2007 | Cohen et al. |
| 7,321,793 B2 | 1/2008 | Ben-Ezra et al. |
| 7,324,853 B2 | 1/2008 | Ayal et al. |
| 7,346,398 B2 | 3/2008 | Gross et al. |
| 7,460,906 B2 | 12/2008 | Libbus |
| 7,561,922 B2 | 7/2009 | Cohen et al. |
| 7,584,004 B2 * | 9/2009 | Caparso et al. ............ 607/118 |
| 7,623,926 B2 | 11/2009 | Rossing et al. |
| 7,627,384 B2 | 12/2009 | Ayal et al. |
| 7,628,750 B2 | 12/2009 | Cohen et al. |
| 7,634,317 B2 | 12/2009 | Ben-David et al. |
| 7,668,602 B2 | 2/2010 | Ben-David et al. |
| 7,734,355 B2 | 6/2010 | Cohen et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,805,203 B2 | 9/2010 | Ben-David et al. |
| 7,809,442 B2 * | 10/2010 | Bolea et al. ............ 607/42 |
| 7,840,266 B2 | 11/2010 | Libbus et al. |
| 7,844,346 B2 | 11/2010 | Cohen et al. |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,904,151 B2 | 3/2011 | Ben-David et al. |
| 7,904,176 B2 | 3/2011 | Ben-Ezra et al. |
| 7,908,008 B2 | 3/2011 | Ben-David et al. |
| 7,996,092 B2 * | 8/2011 | Mrva et al. ............ 607/118 |
| 8,155,757 B1 * | 4/2012 | Neisz et al. ............ 607/118 |
| 8,214,056 B2 * | 7/2012 | Hoffer et al. ............ 607/118 |
| 2002/0099419 A1 | 7/2002 | Cohen et al. |
| 2002/0161415 A1 | 10/2002 | Cohen et al. |
| 2003/0040785 A1 | 2/2003 | Maschino et al. |
| 2003/0045909 A1 | 3/2003 | Gross et al. |
| 2003/0045914 A1 | 3/2003 | Cohen et al. |
| 2003/0050677 A1 | 3/2003 | Gross et al. |
| 2003/0097221 A1 | 5/2003 | Chun et al. |
| 2003/0100933 A1 | 5/2003 | Ayal et al. |
| 2004/0006311 A1 * | 1/2004 | Shchervinsky .......... 604/164.01 |
| 2004/0006331 A1 * | 1/2004 | Shchervinsky ............ 604/541 |
| 2004/0193231 A1 | 9/2004 | Ben-David et al. |
| 2004/0199210 A1 | 10/2004 | Shelchuk |
| 2004/0243182 A1 | 12/2004 | Cohen et al. |
| 2005/0010265 A1 * | 1/2005 | Baru Fassio et al. ........... 607/48 |
| 2005/0065553 A1 | 3/2005 | Ben-Ezra et al. |
| 2005/0131467 A1 | 6/2005 | Boveja |
| 2005/0149154 A1 | 7/2005 | Cohen et al. |
| 2005/0187584 A1 | 8/2005 | Denker et al. |
| 2005/0187586 A1 | 8/2005 | Ben-David et al. |
| 2005/0197675 A1 | 9/2005 | Ben-David et al. |
| 2005/0261672 A1 | 11/2005 | Deem et al. |
| 2005/0267542 A1 | 12/2005 | Ben-David et al. |
| 2005/0273138 A1 | 12/2005 | To et al. |
| 2006/0052831 A1 | 3/2006 | Fukui |
| 2006/0074449 A1 | 4/2006 | Denker et al. |
| 2006/0100668 A1 | 5/2006 | Ben-David et al. |
| 2006/0106441 A1 | 5/2006 | Ayal et al. |
| 2006/0116739 A1 | 6/2006 | Betser et al. |
| 2006/0136024 A1 | 6/2006 | Cohen et al. |
| 2006/0167501 A1 | 7/2006 | Ben-David et al. |
| 2006/0195170 A1 | 8/2006 | Cohen et al. |
| 2006/0206153 A1 | 9/2006 | Libbus et al. |
| 2006/0206154 A1 | 9/2006 | Moffitt et al. |
| 2006/0206155 A1 | 9/2006 | Ben-David et al. |
| 2006/0206159 A1 | 9/2006 | Moffitt et al. |
| 2006/0217772 A1 | 9/2006 | Libbus et al. |
| 2006/0229677 A1 | 10/2006 | Moffitt et al. |
| 2006/0241697 A1 | 10/2006 | Libbus et al. |
| 2006/0241725 A1 | 10/2006 | Libbus et al. |
| 2006/0241733 A1 | 10/2006 | Zhang et al. |
| 2006/0247607 A1 | 11/2006 | Cornelius et al. |
| 2006/0265027 A1 | 11/2006 | Vaingast et al. |
| 2006/0271108 A1 | 11/2006 | Libbus et al. |
| 2006/0271115 A1 | 11/2006 | Ben-Ezra et al. |
| 2006/0271137 A1 * | 11/2006 | Stanton-Hicks ............ 607/118 |
| 2006/0282145 A1 * | 12/2006 | Caparso et al. ............ 607/118 |
| 2007/0150034 A1 * | 6/2007 | Rooney et al. ............ 607/115 |
| 2007/0162079 A1 | 7/2007 | Shemer et al. |
| 2007/0179543 A1 | 8/2007 | Ben-David et al. |
| 2007/0179558 A1 | 8/2007 | Gliner et al. |
| 2007/0203527 A1 | 8/2007 | Ben-David et al. |
| 2007/0239243 A1 | 10/2007 | Moffitt et al. |
| 2007/0255320 A1 * | 11/2007 | Inman et al. ............ 607/2 |
| 2008/0004673 A1 * | 1/2008 | Rossing et al. ............ 607/44 |
| 2008/0007360 A1 | 1/2008 | Hosokawa et al. |

(56) References Cited

U.S. PATENT DOCUMENTS

| | | | |
|---|---|---|---|
| 2008/0021504 | A1 | 1/2008 | McCabe et al. |
| 2008/0046016 | A1 | 2/2008 | Ben-David et al. |
| 2008/0065158 | A1 | 3/2008 | Ben-Ezra et al. |
| 2008/0065184 | A1* | 3/2008 | Hoffer et al. ............... 607/118 |
| 2008/0086180 | A1 | 4/2008 | Ben-Ezra et al. |
| 2008/0086185 | A1 | 4/2008 | Amurthur et al. |
| 2008/0091241 | A1 | 4/2008 | Ben-Ezra et al. |
| 2008/0091245 | A1 | 4/2008 | Ben-Ezra et al. |
| 2008/0109045 | A1 | 5/2008 | Gross et al. |
| 2008/0119898 | A1 | 5/2008 | Ben-David et al. |
| 2008/0125819 | A1 | 5/2008 | Ben-David et al. |
| 2008/0125825 | A1 | 5/2008 | Ben-Ezra et al. |
| 2008/0125827 | A1 | 5/2008 | Ben-David et al. |
| 2008/0132964 | A1 | 6/2008 | Cohen et al. |
| 2008/0132983 | A1 | 6/2008 | Cohen et al. |
| 2008/0140141 | A1 | 6/2008 | Ben-David et al. |
| 2008/0147137 | A1 | 6/2008 | Cohen et al. |
| 2008/0161895 | A1 | 7/2008 | Gross et al. |
| 2008/0172116 | A1* | 7/2008 | Mrva et al. ............... 607/115 |
| 2008/0177338 | A1 | 7/2008 | Ben-David et al. |
| 2008/0234780 | A1 | 9/2008 | Smith et al. |
| 2009/0005845 | A1 | 1/2009 | David et al. |
| 2009/0259315 | A1* | 10/2009 | Banik ............... 623/14.13 |
| 2009/0275996 | A1* | 11/2009 | Burnes et al. ............... 607/2 |
| 2010/0010603 | A1 | 1/2010 | Ben-David et al. |
| 2010/0042186 | A1 | 2/2010 | Ben-David et al. |
| 2010/0042194 | A1 | 2/2010 | Ayal et al. |
| 2010/0047376 | A1* | 2/2010 | Imbeau et al. ............... 425/116 |
| 2010/0241195 | A1* | 9/2010 | Meadows et al. ............... 607/62 |
| 2010/0241207 | A1* | 9/2010 | Bluger ............... 607/118 |
| 2010/0312320 | A1* | 12/2010 | Faltys et al. ............... 607/118 |
| 2011/0160827 | A1* | 6/2011 | Bonde et al. ............... 607/118 |
| 2011/0196445 | A1* | 8/2011 | Bolea et al. ............... 607/42 |
| 2011/0202106 | A1* | 8/2011 | Bolea et al. ............... 607/42 |
| 2012/0095540 | A1* | 4/2012 | Wahlstrand et al. ............... 607/118 |
| 2012/0130463 | A1* | 5/2012 | Ben-David et al. ............... 607/118 |
| 2012/0197371 | A1* | 8/2012 | Neisz et al. ............... 607/118 |

FOREIGN PATENT DOCUMENTS

| | | |
|---|---|---|
| EP | 0 865 800 | 9/1998 |
| EP | 1 785 160 | 5/2007 |
| WO | WO 01/10375 | 2/2001 |
| WO | WO 02/22206 | 3/2002 |
| WO | WO 02/087683 | 11/2002 |
| WO | WO 03/018113 | 3/2003 |
| WO | WO 03/094693 | 11/2003 |
| WO | WO 03/099373 | 12/2003 |
| WO | WO 03/099377 | 12/2003 |
| WO | WO 2004/028624 | 4/2004 |
| WO | WO 2004/047914 | 6/2004 |
| WO | WO 2004/052444 | 6/2004 |
| WO | WO 2004/103455 | 12/2004 |
| WO | WO 2004/110549 | 12/2004 |
| WO | WO 2004/110550 | 12/2004 |
| WO | WO 2006/126201 | 11/2006 |
| WO | WO 2007/053065 | 5/2007 |
| WO | WO 2008/007360 | 1/2008 |

OTHER PUBLICATIONS

An Office Action dated Sep. 28, 2011, which issued during the prosecution of U.S. Appl. No. 12/228,630.

An Office Action dated Jun. 8, 2012, which issued during the prosecution of U.S. Appl. No. 12/228,630.

An Office Action dated Aug. 21, 2012, which issued during the prosecution of U.S. Appl. No. 13/271,720.

An Office Action dated Jul. 30, 2012, which issued during the prosecution of U.S. Appl. No. 11/978,440.

An Official Action dated May 26, 2011, which issued during the prosecution of Applicant's U.S. Appl. No. 12/012,366.

An Official Action dated May 23, 2011, which issued during the prosecution of Applicant's U.S. Appl. No. 11/978,776.

An Official Action dated Jun. 7, 2011, which issued during the prosecution of Applicant's U.S. Appl. No. 12/589,132.

An Extended European Search Report dated Jun. 6, 2011, which issued during the prosecution of Applicant's European Patent Application No. 11002403.

Vincenzi, et al., "Release of autonomic mediators in cardiac tissue by direct subthreshold electrical stimulation", J Pharmacol Exp Ther. Aug. 1963; 141:185-94.

Quan KJ, et al., "Endocardial stimulation of efferent parasympathetic nerves to the atrioventricular node in humans: optimal stimulation sites and the effects of digoxin", Journal of Interventional Cardiac Ekectrophysiology 5:145-152, 2001.

Lemery R et al., "Feasibility study of endocardial mapping of ganglionated plexuses during catheter ablation of atrial fibrillation", Heart Rhythm 3:387-396, 2006.

Wallick DW et al., "Selective AV nodal vagal stimulation improves hemodynamics during acute atrial fibrillation in dogs", Am J Physiol Heart Circ Physiol 281:H1490-H1497, 2001.

Zhang Y et al., "Chronic atrioventricular nodal vagal stimulation: first evidence for long-term ventricular rate control in canine atrial fibrillation model", Circulation 112:2904-2911, 2005.

Schaurete P et al., "Ventricular rate control during atrial fibrillation by cardiac parasympathetic nerve stimulation: A transvenous approach", Journal of the American College of Cardiology 34(7): 2043-2050, 1999.

Schaurete P et al., "Catheter stimulation of cardiac parasympathetic nerves in humans: A novel approach to the cardiac autonomic nervous system", Circulation 104: 2430-2435, 2001.

Schaurete P et al., "Transvenous parasympathetic cardiac nerve stimulation for treatment of tachycardiac atrial fibrillation", Tachycarde Rhythmusstorungen 89:766-773, 2000.

Lazzara R et al., "Selective in situ parasympathetic control of the canine sinuatrial and atrioventricular node ", Circulation Research 32:393-401, 1973.

Chen SA, et al., "Intracardiac stimulation of human parasympathetic nerve fibers induces negative dromotropic effects: implication with the lesions of radiofrequency catheter ablation", Journal of Cardiovascular Electrophysiology 9(3):245-52, 1998.

Bluemel KM, "Parasympathetic postganglionic pathways to the sinoatrial node," J Physiol. 259(5 Pt 2):H1504-10 (1990).

Cooper et al., "Neural effects on sinus rate and atrial ventricular conduction produced by electrical stimulation from a transvenous electrode catheter in the canine right pulmonary artery" Circ Res vol. 46(1):48-57 (1980).

Goldberger JJ et al., "New technique for vagal nerve stimulation," J Neurosci Methods. 91(1-2):109-14 (1999).

Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.

Tarver W B et al., "Clinical experience with a helical bipolar stimulating lead", Pace, vol. 15, October, Part 11 (1992).

Naples GG et al., "A spiral nerve cuff electrode for peripheral nerve stimulation," by IEEE Transactions on Biomedical Engineering, 35(11) (1988).

Fitzpatrick et al., in "A nerve cuff design for the selective activation and blocking of myelinated nerve fibers," Ann Conf. of the IEEE Eng. in Medicine and Biology Soc, 13(2), 906 (1991).

Baratta R et al., "Orderly stimulation of skeletal muscle motor units with tripolar nerve cuff electrode," IEEE Transactions on Biomedical Engineering, 36(8):836-43 (1989).

Deurloo KE et al., "Transverse tripolar stimulation of peripheral nerve: a modelling study of spatial selectivity," Med Biol Eng Comput, 36(1):66-74 (1998).

Takei M et al., "Vagal stimulation prior to atrial rapid pacing protects the atrium from electrical remodeling in anesthetized dogs," Jpn Circ J 65(12):1077-81 (2001).

Hayashi H et al., "Different effects of class Ic and III antiarrhythmic drugs on vagotonic atrial fibrillation in the canine heart," Journal of Cardiovascular Pharmacology 31:101-107 (1998).

Masato Tsuboi et al., "Inotropic, chronotropic, and dromotropic effects mediated via parasympathetic ganglia in the dog heart," Am J Physiol Heart Circ Physiol 279: H1201-H1207 (2000).

Wijffels MC et al., "Atrial fibrillation begets atrial fibrillation," Circulation 92:1954-1968 (1995).

Sweeney JD et al., "An asymmetric two electrode cuff for generation of unidirectionally propagated action potentials," IEEE Transactions on Biomedical Engineering, vol. BME-33(6) (1986).

(56) References Cited

OTHER PUBLICATIONS

Ungar IJ et al., "Generation of unidirectionally propagating action potentials using a monopolar electrode cuff," Annals of Biomedical Engineering, 14:437-450 (1986).
van den Honert C et al., "A technique for collision block of peripheral nerve: Frequency dependence," MP-12, IEEE Trans. Biomed. Eng. 28:379-382 (1981).
van den Honert C et al., "Generation of unidirectionally propagated action potentials in a peripheral nerve by brief stimuli," Science, 206:1311-1312 (1979).
Randall WC ed., Neural Regulation of the Heart, Oxford University Press (1977), particularly pp. 100-106.
Rijkhoff NJ et al., "Orderly recruitment of motoneurons in an acute rabbit model," Ann. Conf. of the IEEE Eng., Medicine and Biology Soc., 20(5):2564 (1998).
Sweeney JD et al., "A nerve cuff technique for selective excitation of peripheral nerve trunk regions," IEEE Transactions on Biomedical Engineering, 37(7) (1990).
Martin PJ et al., "Phasic effects of repetitive vagal stimulation on atrial contraction," Circ. Res. 52(6):657-63 (1983).
Manfredi M, "Differential block of conduction of larger fibers in peripheral nerve by direct current," Arch. Ital. Biol., 108:52-71 (1970).
Wang H et al., "Nicotinic acetylcholine receptor alpha-7 subunit is an essential regulator of inflammation," Nature 421:384-388 (2003).
Waninger MS et al., "Electrophysiological control of ventricular rate during atrial fibrillation," PACE 23:1239-1244 (2000).
Vanoli E et al., "Vagal stimulation and prevention of sudden death in conscious dogs with a healed myocardial infarction," Circ Res 68(5):1471-81 (1991).
Veraart C et al., "Selective control of muscle activation with a multipolar nerve cuff electrode," IEEE Trans Biomed Eng, 40(7):640-53 (1993).
Li D et al., "Promotion of Atrial Fibrillation by Heart Failure in Dogs: Atrial Remodeling of a Different Sort," Circulation 100(1):87-95 (1999).
Morady F et al., "Effects of resting vagal tone on accessory atrioventricular connections," Circulation 81(1):86-90 (1990).
Mushahwar VK et al., "Muscle recruitment through electrical stimulation of the lumbo-sacral spinal cord," IEEE Trans Rehabil Eng, 8(1):22-9 (2000).
Rijkhoff NJ et al., "Acute animal studies on the use of anodal block to reduce urethral resistance in sacral root stimulation," IEEE Transactions on Rehabilitation Engineering, 2(2):92 (1994).
Stramba-Badiale M et al., "Sympathetic-Parasympathetic Interaction and Accentuated Antagonism in Conscious Dogs," American Journal of Physiology 260 (2Pt 2):H335-340 (1991).
Kamath et al., in "Effect of vagal nerve electrostimulation on the power spectrum of heart rate variability in man," Pacing Clin Electrophysiol 15:235-43 (1992).
Kwan H et al., "Cardiovascular adverse drug reactions during initiation of antiarrhythmic therapy for atrial fibrillation," Can J Hosp Pharm 54:10-14 (2001).
Garrigue S et al., "Post-ganglionic vagal stimulation of the atrioventricular node reduces ventricular rate during atrial fibrillation," PACE 21(4), 878 (Part II) (1998).
Goodall EV et al., "Position-selective activation of peripheral nerve fibers with a cuff electrode," IEEE Trans Biomed Eng, 43(8):851-6 (1996).
Grill WM et al., "Inversion of the current-distance relationship by transient depolarization," IEEE Trans Biomed Eng, 44(1):1-9 (1997).
Higgins CB, "Parasympathetic control of the heart," Pharmacol. Rev. 25:120-155 (1973).
Jidéus L, "Atrial fibrillation after coronary artery bypass surgery: A study of causes and risk factors," Acta Universitatis Upsaliensis, Uppsala, Sweden (2001).
Jones, JFX et al., "Heart rate responses to selective stimulation of cardiac vagal C fibres in anaesthetized cats, rats and rabbits," J Physiol 489 (Pt 1):203-14 (1995).

Akselrod S et al., "Power spectrum analysis of heart rate fluctuation: a quantitative probe of beat-to-beat cardiovascular control," Science 213: 220-222 (1981).
Billette J et al., "Roles of the AV junction in determining the ventricular response to atrial fibrillation," Can J Physiol Pharamacol 53(4)575-85 (1975).
Borovikova LV et al., "Vagus nerve stimulation attenuates the systemic inflammatory response to endotoxin," Nature 405(6785):458-62 (2000).
De Ferrari GM, "Vagal reflexes and survival during acute myocardial ischemia in conscious dogs with healed myocardial infarction," Am J Physiol 261(1 Pt 2):H63-9 (1991).
Hoffer JA et al., "How to use nerve cuffs to stimulate, record or modulate neural activity," in Neural Prostheses for Restoration of Sensory and Motor Function, Chapin JK et al. (Eds.), CRC Press (1st edition, 2000).
van den Honert C et al., "A technique for collision block of peripheral nerve: Single stimulus analysis," MP-11, IEEE Trans. Biomed. Eng. 28:373-378 (1981).
An Office Action dated Dec. 8, 2009, which issued during the prosecution of Applicant's U.S. Appl. No. 11/347,120.
An Office Action dated Oct. 24, 2008, which issued during the prosecution of Applicant's U.S. Appl. No. 11/022,011.
A Supplementary European Search Report dated Nov. 11, 2009, which issued during the prosecution of Applicant's European Patent Application No. EP 03723040.
A European Search Report dated Aug. 27, 2009, which issued during the prosecution of Applicant's European Patent Application No. EP 09 25 1749.
A Supplementary European Search Report dated Aug. 16, 2010, which issued during the prosecution of Applicant's European Patent Application No. 03725560.
An Examination Report dated Feb. 7, 2011, which issued during the prosecution of Applicant's European Patent Application No. 03725560.
An Office Action dated Jan. 21, 2011, which issued during the prosecution of Applicant's U.S. Appl. No. 12/589,132.
An Examination Report dated Aug. 13, 2010, which issued during the prosecution of Applicant's European Patent Application No. EP 03 72 3040.
A Supplementary European Search Report dated Dec. 19, 2008, which issued during the prosecution of Applicant's European Patent Application No. 02716294.0.
An Examination Report dated Apr. 3, 2009, which issued during the prosecution of Applicant's European Patent Application No. 02716294.0.
An Examination Report dated Oct. 6, 2010, which issued during the prosecution of Applicant's European Patent Application No. 02716294.0.
An Office Action dated Jun. 7, 2011, which issued during the prosecution of Applicant's U.S. Appl. No. 12/589,132.
An Office Action dated May 23, 2011, which issued during the prosecution of Applicant's U.S. Appl. No. 11/978,776.
An Office Action dated Jan. 3, 2011, which issued during the prosecution of Applicant's U.S. Appl. No. 11/978,776.
An International Search Report dated Nov. 16, 2004, which issued during the prosecution of Applicant's PCT/IL04/00440.
An International Search Report dated Dec. 23, 2002, which issued during the prosecution of Applicant's PCT/IL02/00068.
An International Search Report dated Nov. 13, 2003, which issued during the prosecution of Applicant's PCT/IL03/00430.
An Examination Report dated May 25, 2009, which issued during the prosecution of Applicant's European Patent Application No. 06255816.8.
A European Search Report dated Oct. 19, 2007, which issued during the prosecution of Applicant's European Patent Application No. 06255816.8.
An International Search Report and Written Opinion issued on Jul. 11, 2013 in PCT/IL2013/050286.
An office action issued on Jul. 23, 2013 in U.S. Appl. No. 12/947,608.

* cited by examiner

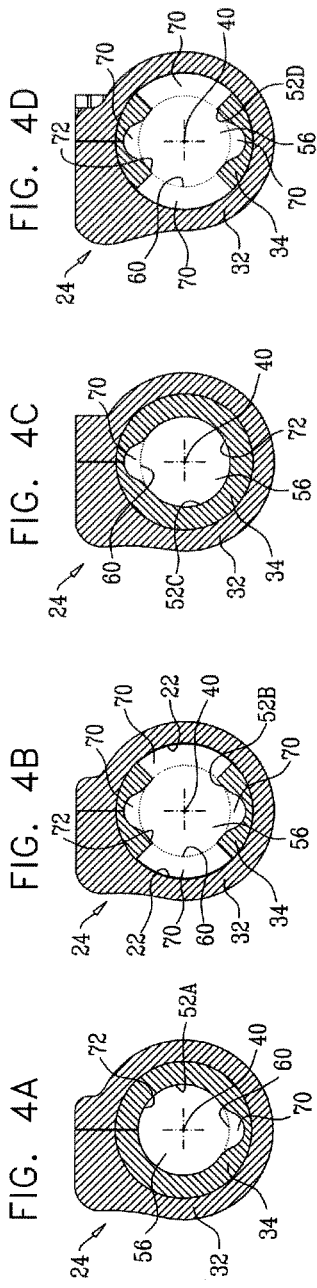

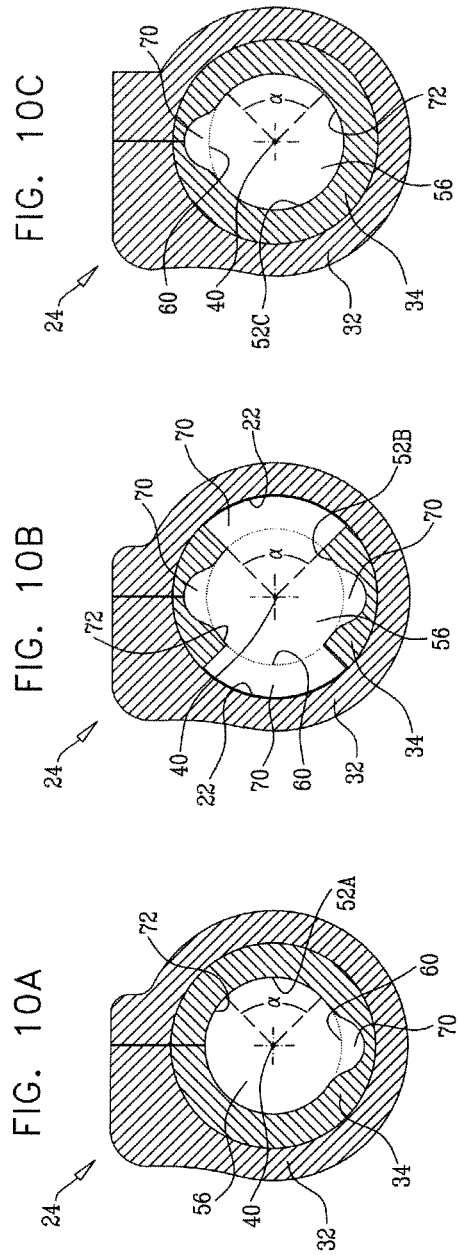

US 8,565,896 B2

ELECTRODE CUFF WITH RECESSES

FIELD OF THE APPLICATION

The present invention relates generally to electrical stimulation of tissue, and specifically to methods and devices for regulating the stimulation of nerves or other tissue.

BACKGROUND

A number of patents and articles describe methods and devices for stimulating nerves to achieve a desired effect. Often these techniques include a design for an electrode or electrode cuff.

SUMMARY OF THE APPLICATION

In some embodiments of the present invention, an electrode assembly for applying current to tubular body tissue, such as a nerve, comprises one or more electrode contact surfaces fixed to a cuff. The cuff is shaped so as to define a plurality of recesses that extend radially outwardly from an innermost surface of the cuff surrounding a longitudinal axis of the cuff. Typically, the cuff is recessed in at least one radially outward direction at every longitudinal location along its entire length. The recesses may serve to prevent damage to the nerve by allowing the nerve to swell in at least one radial direction into at least one of the recesses, along the entire length of the cuff. Providing the recesses generally does not have a material impact on the activation function achieved by the electrode assembly.

Typically, each of the recesses has a length along the cuff that is less than the entire length of the cuff, e.g., less than 50% or 25% of the length of the cuff. This design generally prevents migration of the nerve over time into the recesses, away from the center of the cuff, as might occur if any of the recesses extended along the entire length, or even most of the length, of the cuff. Holding the cuff in position around the nerve helps maintain good electrical contact between the electrical contact surfaces and the nerve. In addition, because longitudinally adjacent recesses extend in different radially directions, the recesses do not provide a continuous path for current applied by the electrode contact surfaces to pass through the cuff without entering the nerve.

The cuff is typically shaped such that each perpendicular cross section thereof includes one or more portions that coincide with the innermost surface of the cuff. These non-recessed portions serve in part to hold the cuff in position around the nerve. At the same time, the recesses provide space into which the nerve can swell in varying radial directions along the entire length of the cuff, thereby minimizing any damage the cuff may cause to the nerve. Some of these non-recessed portions further serve in part to electrically isolate longitudinally adjacent recesses from each other along the longitudinal axis of the cuff.

In the present application, including in the claims, a "perpendicular cross section" is a planar cross section perpendicular to the longitudinal axis of the cuff.

For some applications, at least two of the recesses extend radially outwardly in different radial directions, such as in opposite radial directions. Typically, at least two of the perpendicular cross sections of the cuff define respective inner closed curves having shapes that differ from one other, when orientation and position of the perpendicular cross sections with respect to the cuff are preserved. For some applications, the inner closed curves of the at least two of the perpendicular cross sections would cross, and not merely intersect, one another if superimposed while preserving orientation and position of the perpendicular cross sections with respect to the cuff. In contrast, in some other nerve cuffs having recesses, the inner curves of the perpendicular cross sections defining the recesses merely have a larger diameter than the inner curves of the non-recessed perpendicular cross sections, but have the same shape (e.g., circular shape).

For some applications, one or more of the recesses have respective electrode contact surfaces coupled therein, such that the electrode contact surfaces are not in physical contact with the nerve when the cuff is placed around the nerve. In addition, one or more of the recesses may not have an electrode contact surface coupled therein. Because the recesses typically do not extend along the entire length of the cuff, electrode contact surfaces coupled within different recesses are electrically isolated from one another along the longitudinal axis of the cuff. Alternatively or additionally, one or more of the electrode contact surfaces are coupled to respective portions of the innermost, non-recessed surface of the cuff, such that the electrode contact surfaces are in physical contact with the nerve when the cuff is placed around the nerve.

As mentioned above, the cuff may define a plurality of planar cross sections perpendicular to the longitudinal axis, which are distributed continuously along the entire length of the cuff. The perpendicular cross sections may define respective inner closed curves surrounding the longitudinal axis. These inner closed curves, if superimposed while preserving orientation and position of the perpendicular cross sections with respect to the cuff, would together define the innermost closed curve surrounding the longitudinal axis, which is mentioned above. For some applications, this innermost closed curve is elliptical, such as circular.

There is therefore provided, in accordance with an application of the present invention, apparatus including an electrode assembly, which includes:

one or more electrode contact surfaces; and a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of planar cross sections perpendicular to the longitudinal axis, distributed continuously along an entire length of the cuff along the longitudinal axis, such that the perpendicular cross sections define respective inner closed curves that together define an inner surface that defines and completely surrounds a volume that extends along the entire length of the cuff, wherein the inner closed curves of at least two of the perpendicular cross sections would cross, and not merely intersect, one another if superimposed while preserving orientation and position of the perpendicular cross sections with respect to the cuff.

For some applications, all of the inner closed curves, if superimposed while preserving orientation and position of the perpendicular cross sections with respect to the cuff, would together define a combined innermost closed curve, and the inner closed curves respectively defined by the perpendicular cross sections enclose respective areas, each of which areas is greater than an area enclosed by the combined innermost closed curve.

For some applications, the entire length of the cuff is between 1 and 40 mm. Alternatively or additionally, for some applications, the volume has a volume of between 10 and 5000 mm3.

For some applications, the cuff is shaped so as to define a plurality of longitudinal segments, distributed continuously along the entire length of the cuff; the segments are shaped so as to define respective ones of the inner closed curves, such that the inner closed curve of each of the segments is of uniform shape along the segment; each of the inner closed curves of at least four of the longitudinal segments has a different shape, and not merely a different size, from the inner closed curve of at least one adjacent longitudinal segment, when orientation and position of the segments with respect to the cuff are preserved; and the at least three segments have respective lengths, measured in parallel with the longitudinal axis, each of which is at least 0.1 mm. For some applications, the inner closed curve of each of the at least four segments is of uniform size along the segment. Alternatively or additionally, for some applications, the inner closed curve of each of at least one of the at least four segments is of non-uniform size along the segment.

For some applications, a first set of a plurality of the perpendicular cross sections contiguous to one another define a first segment of the cuff, a second set of a plurality of the perpendicular cross sections contiguous to one another define a second segment of the cuff, the first and second segments have respective lengths, measured in parallel with the longitudinal axis, each of which is at least 0.1 mm, the first and second segments do not overlap each other lengthwise along the cuff, at least one of the electrode contact surfaces is fixed to the inner surface at the first segment, and none of the electrode contact surfaces is fixed to the inner surface at the second segment. For some applications, all of the inner closed curves defined by the perpendicular cross sections of the first set are identical to one another in shape and size, when orientation and position of the perpendicular cross sections with respect to the cuff are preserved. For some applications, all of the inner closed curves defined by the perpendicular cross sections of the second set are identical to one another in shape and size, when orientation and position of the perpendicular cross sections with respect to the cuff are preserved, and the inner closed curves defined by the perpendicular cross sections of the first set have different shapes, and not merely different sizes, from the inner closed curves defined by the perpendicular cross sections of the second set, when orientation and position of the perpendicular cross sections with respect to the cuff are preserved.

For some applications, the cuff is configured to assume the open and closed positions by defining a slit therethrough that extends along the entire length of the cuff.

For some applications, all of the inner closed curves, if superimposed while preserving orientation and position of the perpendicular cross sections with respect to the cuff, would together define a combined innermost closed curve, and at least a first one of the inner closed curves extends radially outwardly from the combined innermost closed curve in a first radial direction, and at least a second one of the inner closed curves, different from the first inner closed curve, extends radially outwardly from the combined innermost closed curve in a second radial direction different from the first radial direction. For example, the first and second radial directions may be opposite each other.

For some applications, all of the inner closed curves, if superimposed while preserving orientation and position of the perpendicular cross sections with respect to the cuff, would together define a combined innermost closed curve, and each of the inner closed curves partially coincides with the combined innermost closed curve.

There is further provided, in accordance with an application of the present invention, apparatus including an electrode assembly, which includes:
 one or more electrode contact surfaces; and
 a cuff, to which the electrode contact surfaces are fixed, and which: (a) includes an electrically insulating material, (b) has a longitudinal axis, (c) is configured to assume open and closed positions, and (d) when in the closed position, is shaped so as to define:
 (i) a plurality of planar cross sections perpendicular to the longitudinal axis, distributed continuously along an entire length of the cuff along the longitudinal axis, such that the perpendicular cross sections define respective inner closed curves surrounding the longitudinal axis, which inner closed curves define and enclose respective inner cross-sectional regions,
 wherein an intersection of the cross-sectional regions, if the cross-sectional regions were to be superimposed while preserving orientation and position of the cross-sectional regions with respect to the cuff, would define a combined inner cross-sectional region, which, if extended along the entire length of the cuff, would define a combined innermost volume, and
 (ii) a plurality of recesses that are recessed radially outwardly from the combined innermost volume, each of which recesses extends along the longitudinal axis of the cuff and has a greatest length, measured in parallel with the longitudinal axis, that is less than 50% of the entire length of the cuff,
 wherein the inner closed curves enclose respective areas, each of which areas is greater than an area of the combined inner cross-sectional region.

For some applications, the entire length of the cuff is between 1 and 40 mm.

For some applications, the cuff is shaped such that the combined inner cross-sectional region is elliptical, for example, circular.

For some applications, a periphery of the combined inner cross-sectional region defines a combined innermost closed curve, and each of the inner closed curves coincides with the combined innermost closed curve at a portion of, but not all, angles with respect to the longitudinal axis.

For some applications, first and second ones of the recesses overlap each other lengthwise along the cuff, and do not overlap each other anglewise with respect to the longitudinal axis. For some applications, a length of the overlap between the first and second recesses, measured in parallel with the longitudinal axis of the cuff, is at least 0.1 mm.

For some applications, at least a first one of the inner closed curves extends radially outwardly from the combined innermost volume in a first radial direction, and at least a second one of the inner closed curves, different from the first inner closed curve, extends radially outwardly from the combined innermost volume in a second radial direction different from the first radial direction. For example, the first and second radial directions may be opposite each other.

For some applications, each of the recesses has a length, measured in parallel with the longitudinal axis, of at least 0.1 mm.

For some applications, the cuff is configured to assume the open and closed positions by defining a slit therethrough that extends along the entire length of the cuff.

For some applications, at least one of the electrode contact surfaces is fixed within one of the recesses.

For some applications, a first set of a plurality of the perpendicular cross sections contiguous to one another define a first segment of the cuff; a second set of a plurality of the perpendicular cross sections contiguous to one another define a second segment of the cuff; the first and second segments have respective lengths, measured in parallel with the longitudinal axis, each of which is at least 0.1 mm; the first and second segments do not overlap each other lengthwise along the cuff; at least one of the electrode contact surfaces is fixed to an inner surface of the first segment; and none of the electrode contact surfaces is fixed to an inner surface of the second segment.

For some applications:

13 sets of pluralities of the perpendicular cross sections define 13 segments of the cuff, respectively, such that the perpendicular cross sections are contiguous within each of the sets, and the sets are arranged in numerical order from a first set to a thirteenth set along the cuff, such that none of the segments overlap one other lengthwise along the cuff, the 13 segments have respective first through thirteenth lengths, measured in parallel with the longitudinal axis, each of which is at least 0.1 mm, the inner closed curves of the first, fifth, ninth, and thirteenth segments have the same shape as one another, while preserving orientation and position of the inner closed curves with respect to the cuff, the inner closed curves of the second, fourth, sixth, tenth, and twelfth segments have the same shape as one another, while preserving orientation and position of the inner closed curves with respect to the cuff, the inner closed curves of the third, seventh, and eleventh segments have the same shape as one another, while preserving orientation and position of the inner closed curves with respect to the cuff, the inner closed curve of the eighth segment has a shape that is different from the shapes of the inner closed curves of the other segments, while preserving orientation and position of the inner closed curves with respect to the cuff, respective ones of the electrode contact surfaces are fixed within the recesses defined by the second, fourth, sixth, tenth, and twelfth segments, and none of the electrode contact surfaces is fixed within the recesses defined by the first, third, fifth, seventh, eighth, ninth, eleventh, and thirteenth segments.

For some applications, the first, fifth, ninth, and thirteenth segments define respective ones of the recesses that extend generally in a first radial direction, and the third, seventh, and eleventh segments define respective ones of the recesses that extend generally in a second radial direction different from the first radial direction. Alternatively or additionally, for some applications, the first through thirteenth lengths are 0.8 mm, 0.7 mm, 0.8 mm, 0.7 mm, 1.6 mm, 1.1 mm, 0.8 mm, 1.4 mm, 0.8 mm, 0.7 mm, 1.2 mm, 0.7 mm, and 0.8 mm, respectively.

For some applications:

13 sets of pluralities of the perpendicular cross sections define 13 segments of the cuff, respectively, such that the perpendicular cross sections are contiguous within each of the sets, and the sets are arranged in numerical order from a first set to a thirteenth set along the cuff, such that none of the segments overlap one other lengthwise along the cuff, the 13 segments have respective first through thirteenth lengths, measured in parallel with the longitudinal axis, each of which is at least 0.1 mm, respective ones of the electrode contact surfaces are fixed within the recesses defined of the second, fourth, sixth, tenth, and twelfth segments, none of the electrode contact surfaces is fixed within the recesses defined by the first, third, fifth, seventh, eighth, ninth, eleventh, and thirteenth segments, the apparatus further includes a control unit, which configures the electrode contact surface fixed in the recess of the fourth segment to function as an anode, and the electrode contact surfaces fixed within the recesses of the sixth and tenth segments to function as cathodes, and the electrode contact surfaces fixed within the recesses of the second and twelfth segments are electrically device-coupled to each other, and are electrically device-coupled to neither the control unit nor an energy source.

For some applications:

13 sets of pluralities of the perpendicular cross sections define 13 segments of the cuff, respectively, such that the perpendicular cross sections are contiguous within each of the sets, and the sets are arranged in numerical order from a first set to a thirteenth set along the cuff, such that none of the segments overlap one other lengthwise along the cuff, the 13 segments have respective first through thirteenth lengths, measured in parallel with the longitudinal axis, each of which is at least 0.1 mm, respective ones of the electrode contact surfaces are fixed within the recesses defined of the second, fourth, sixth, tenth, and twelfth segments, none of the electrode contact surfaces is fixed within the recesses defined by the first, third, fifth, seventh, eighth, ninth, eleventh, and thirteenth segments, the apparatus further includes a control unit, which configures the electrode contact surface fixed in the recess of the fourth segment to function as an cathode, and the electrode contact surfaces fixed within the recesses of the sixth and tenth segments to function as anodes, and the electrode contact surfaces fixed within the recesses of the second and twelfth segments are electrically device-coupled to each other, and are electrically device-coupled to neither the control unit nor an energy source.

There is still further provided, in accordance with an application of the present invention, apparatus placeable around tubular body tissue, the apparatus including an electrode assembly, which includes:

one or more electrode contact surfaces; and a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of recesses that are recessed radially outwardly from the tubular body tissue if the cuff is placed therearound, such that the cuff is recessed at every longitudinal location along an entire length of the cuff along the longitudinal axis, and each of the recesses extends along the longitudinal axis of the cuff and has a greatest length, measured in parallel with the longitudinal axis, that is less than 50% of the entire length of the cuff.

For some applications, the entire length of the cuff is between 1 and 40 mm.

For some applications, the cuff is shaped so as to come in contact with the tubular body tissue at a portion of, but not all, angles with respect to the longitudinal axis, at every longitudinal location along the entire length of the cuff, if the cuff is placed around the tubular body tissue in the closed position.

For some applications, the tubular body tissue is a nerve, and the cuff is configured to be applied to the nerve.

For some applications, at least one of the electrode contact surfaces is fixed within one of the recesses.

There is additionally provided, in accordance with an application of the present invention, apparatus placeable around an elliptical cylinder having a major axis that is between 1 and 8 mm and a minor axis that is between 0.5 and 6 mm, the apparatus including an electrode assembly, which includes:

one or more electrode contact surfaces; and a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of recesses that are recessed radially outwardly from the cylinder if the cuff is placed therearound, such that the cuff is recessed at every longitudinal location along an entire length of the cuff along the longitudinal axis, and each of the recesses extends along the longitudinal axis of the cuff and has a greatest length, measured in parallel with the longitudinal axis, that is less than 50% of the entire length of the cuff.

For some applications, the entire length of the cuff is between 1 and 40 mm.

For some applications, the cuff is shaped so as to come in contact with the cylinder at a portion of, but not all, angles with respect to the longitudinal axis, at every longitudinal location along the entire length of the cuff, if the cuff is placed around the cylinder in the closed position.

For some applications, at least one of the electrode contact surfaces is fixed within one of the recesses.

There is yet additionally provided, in accordance with an application of the present invention, apparatus including an electrode assembly, which includes:

one or more electrode contact surfaces; and a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of longitudinal segments, which are (i) distributed continuously along an entire length of the cuff along the longitudinal axis, and (ii) shaped so as to define respective inner closed curves surrounding the longitudinal axis, such that the inner closed curve of each of the segments is of uniform shape along the segment, wherein each of the inner closed curves of at least four of the longitudinal segments has a different shape, and not merely a different size, from the inner closed curve of at least one adjacent longitudinal segment, when orientation and position of the segments with respect to the cuff are preserved, the at least four segments having respective lengths, measured in parallel with the longitudinal axis, each of which is at least 0.1 mm.

For some applications, the inner closed curve of each of the at least four segments is of uniform size along the segment.

For some applications, the inner closed curve of each of at least one of the at least four segments is of non-uniform size along the segment.

There is also provided, in accordance with an application of the present invention, apparatus including an electrode assembly, which includes:

one or more electrode contact surfaces; and a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of longitudinal segments, which are (i) distributed continuously along an entire length of the cuff along the longitudinal axis, and (ii) shaped so as to define respective inner closed curves surrounding the longitudinal axis, such that the inner closed curve of each of the segments is of uniform shape along the segment, wherein each of the inner closed curves of at least three of the longitudinal segments has a different shape, and not merely a different size, from the inner closed curve of at least one adjacent longitudinal segment, when orientation and position of the segments with respect to the cuff are preserved, the at least three segments having respective lengths, measured in parallel with the longitudinal axis, each of which is at least 0.1 mm and no more than 50% of the entire length of the cuff.

For some applications, the inner closed curve of each of the at least three segments is of uniform size along the segment.

For some applications, the inner closed curve of each of at least one of the at least three segments is of non-uniform size along the segment.

For some applications, each of the inner closed curves of at least four of the longitudinal segments has a different shape, and not merely a different size, from the inner closed curve of at least one adjacent longitudinal segment, when the orientation and position of the segments with respect to the cuff are preserved, the at least four segments having respective lengths, measured in parallel with the longitudinal axis, each of which is at least 0.1 mm.

For some applications, the entire length of the cuff is between and 40 mm.

For some applications, each of the inner closed curves of at least five (e.g., at least ten) of the longitudinal segments has a different shape, and not merely a different size, from the inner closed curve of at least one adjacent longitudinal segment, when the orientation and position of the segments with respect to the cuff are preserved, the at least five (e.g., at least ten) segments having respective lengths, measured in parallel with the longitudinal axis, each of which is at least 0.1 mm.

For some applications, the inner closed curves of at least two of the longitudinal segments that are not longitudinally adjacent to each other have the same shape, when the orientation and position of the segments with respect to the cuff are preserved.

For some applications, the one or more electrode contact surfaces are fixed to exactly one of the segments.

For some applications, at least one of the electrode contact surfaces is fixed to an inner surface of a first one of the segments, and none of the electrode contact surfaces is fixed to an inner surface of at least a second one of the segments. For some applications, at least one of the electrode contact surfaces is fixed to an inner surface of a third one of the segments, and the first and third segments are longitudinally separated by the at least a second one of the segments.

For some applications, all of the inner closed curves, if superimposed while preserving orientation and position of the inner closed curves with respect to the cuff, would together define a combined innermost closed curve, and the inner closed curves respectively defined by the inner closed curves enclose respective areas, each of which areas is greater than an area enclosed by the combined innermost closed curve.

For some applications, all of the inner closed curves, if superimposed while preserving orientation and position of the inner closed curves with respect to the cuff, would together define a combined innermost closed curve, and each of the inner closed curves coincides with the combined innermost closed curve at a portion of, but not all, angles with respect to the longitudinal axis.

For some applications, the cuff is configured to assume the open and closed positions by defining a slit therethrough that extends along the entire length of the cuff.

There is further provided, in accordance with an application of the present invention, apparatus including an electrode assembly, which includes:

a plurality of electrode contact surfaces: and a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of longitudinal segments, distributed continuously along an entire length of the cuff along the longitudinal axis, the segments having respective planar cross sections perpendicular to the longitudinal axis, which perpendicular cross sections define respective inner closed curves surrounding the longitudinal axis, such that the inner closed curve of each of the segments is of uniform shape along the segment, wherein the inner closed curves, if superimposed while preserving orientation and position of the inner closed curves with respect to the cuff, would together define a combined innermost closed curve surrounding the longitudinal axis, which combined innermost closed curve, if extended along the entire length of the cuff, would define a combined innermost volume, wherein a first one of the segments is shaped so as to define one or more first recesses that are recessed radially outward from the combined innermost volume, wherein a second one of the segments is shaped so as to define one or more second recesses that are recessed radially outward from the combined innermost volume, wherein a first one of the electrode contact surfaces is fixed within one of the first recesses, the one of the first recesses being recessed radially outward from the combined innermost volume at a first range of angles with respect to the longitudinal axis, wherein a second one of the electrode contact surfaces is fixed within one of the second recesses, the one of the second recesses being recessed radially outward from the combined innermost volume at a second range of angles with respect to the longitudinal axis, wherein one or more third ones of the segments longitudinally separate the first segment from the second segment, and each of the respective inner closed curves of the third segments coincides with the combined innermost closed curve at both the first and second ranges of angles with respect to the longitudinal axis, and wherein the inner closed curves of the third segments enclose respective areas, each of which areas is greater than an area enclosed by the combined innermost closed curve.

For some applications, the inner closed curve of each of the segments is of uniform size along the segment.

For some applications, the inner closed curve of each of at least one of the segments is of non-uniform size along the segment.

For some applications, the entire length of the cuff is between 1 and 40 mm.

For some applications, the first and second ranges of angles coincide.

For some applications, none of the electrode contact surfaces is fixed to the one or more third segments.

For some applications, the one or more first recesses include the one of the first recesses and at least one additional first recess. For some applications, none of the electrode contact surfaces is fixed in the at least one additional first recess. For some applications, at least one of the electrode contact surfaces is fixed in the at least one additional first recess.

For some applications, the segments have respective lengths, measured in parallel with the longitudinal axis, each of which is at least 0.1 mm.

For some applications, all of the electrode contact surfaces are recessed away from the combined innermost volume.

For some applications, the plurality of electrode contact surfaces includes at least three electrode contact surfaces.

For some applications, the inner closed curves enclose respective areas, each of which areas is greater than an area enclosed by the combined innermost closed curve.

For some applications, each of the inner closed curves coincides with the combined innermost closed curve at a portion of, but not all, angles with respect to the longitudinal axis.

For some applications, the cuff is shaped such that the combined innermost closed curve is elliptical, for example, circular.

For some applications, the cuff is configured to assume the open and closed positions by defining a slit therethrough that extends along the entire length of the cuff.

There is still further provided, in accordance with an application of the present invention, apparatus placeable around tubular body tissue, including an electrode assembly, which includes:

a plurality of electrode contact surfaces; and a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of longitudinal segments, distributed continuously along an entire length of the cuff along the longitudinal axis, the segments having respective planar cross sections perpendicular to the longitudinal axis, which perpendicular cross sections define respective inner closed curves surrounding the longitudinal axis, such that the inner closed curve of each of the segments is of uniform shape along the segment, wherein a first one of the segments is shaped so as to define one or more first recesses that are recessed radially outward from the tubular body tissue if the cuff is placed therearound, wherein a second one of the segments is shaped so as to define one or more second recesses that are recessed radially outward from the tubular body tissue if the cuff is placed therearound, wherein a first one of the electrode contact surfaces is fixed within one of the first recesses, the one of the first recesses being recessed radially outward from the tubular body tissue, if the cuff is placed therearound, at a first range of angles with respect to the longitudinal axis, wherein a second one of the electrode contact surfaces is fixed within one of the second recesses, the one of the second recesses being recessed radially outward from the tubular body tissue, if the cuff is placed therearound, at a second range of angles with respect to the longitudinal axis, wherein one or more third ones of the segments longitudinally separate the first segment from the second segment, and each of the respective inner closed curves of the third segments coincides with the combined innermost closed curve at both the first and second ranges of angles with respect to the longitudinal axis, and wherein the inner closed curves of the third segments enclose respective areas, each of which areas is greater than a perpendicular cross-sectional area of the tubular body tissue.

For some applications, the inner closed curve of each of the segments is of uniform size along the segment.

For some applications, the inner closed curve of each of at least one of the segments is of non-uniform size along the segment.

For some applications, the entire length of the cuff is between 1 and 40 mm.

For some applications, the first and second ranges of angles coincide.

For some applications, none of the electrode contact surfaces is fixed to the one or more third segments.

For some applications, the segments have respective lengths, measured in parallel with the longitudinal axis, each of which is at least 0.1 mm.

For some applications, the tubular body tissue is a nerve, and the cuff is configured to be applied to the nerve.

For some applications, all of the electrode contact surfaces are recessed away from the tubular body tissue, if the cuff is placed therearound.

There is additionally provided, in accordance with an application of the present invention, apparatus placeable around an elliptical cylinder having a major axis that is between 1 and 8 mm and a minor axis that is between 0.5 and 6 mm, the apparatus including an electrode assembly, which includes:

a plurality of electrode contact surfaces; and a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of longitudinal segments, distributed continuously along an entire length of the cuff along the longitudinal axis, the segments having respective planar cross sections perpendicular to the longitudinal axis, which perpendicular cross sections define respective inner closed curves surrounding the longitudinal axis, such that the inner closed curve of each of the segments is of uniform shape along the segment, wherein a first one of the segments is shaped so as to define one or more first recesses that are recessed radially outward from the cylinder if the cuff is placed therearound, wherein a second one of the segments is shaped so as to define one or more second recesses that are recessed radially outward from the cylinder if the cuff is placed therearound, wherein a first one of the electrode contact surfaces is fixed within one of the first recesses, the one of the first recesses being recessed radially outward from the cylinder, if the cuff is placed therearound, at a first range of angles with respect to the longitudinal axis, wherein a second one of the electrode contact surfaces is fixed within one of the second recesses, the one of the second recesses being recessed radially outward from the cylinder, if the cuff is placed therearound, at a second range of angles with respect to the longitudinal axis, wherein one or more third ones of the segments longitudinally separate the first segment from the second segment, and each of the respective inner closed curves of the third segments coincides with the combined innermost closed curve at both the first and second ranges of angles with respect to the longitudinal axis, and, and wherein the inner closed curves of the third segments enclose respective areas, each of which areas is greater than a perpendicular cross-sectional area of the cylinder.

For some applications, the inner closed curve of each of the segments is of uniform size along the segment.

For some applications, the inner closed curve of each of at least one of the segments is of non-uniform size along the segment.

For some applications, the entire length of the cuff is between 1 and 40 mm.

For some applications, the first and second ranges of angles coincide.

There is yet additionally provided, in accordance with an application of the present invention, a method including:

providing an electrode assembly that includes (1) one or more electrode contact surfaces, and (2) a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of planar cross sections perpendicular to the longitudinal axis, distributed continuously along an entire length of the cuff along the longitudinal axis, such that the perpendicular cross sections define respective inner closed curves that together define an inner surface that defines and completely surrounds a volume that extends along the entire length of the cuff, wherein the inner closed curves of at least two of the perpendicular cross sections would cross, and not merely intersect, one another if superimposed while preserving orientation and position of the perpendicular cross sections with respect to the cuff;

while the cuff is in the open position, placing the electrode assembly around tubular body tissue of a subject; and coupling the cuff to the tubular body tissue by causing the cuff to assume the closed position.

For some applications, providing the electrode assembly includes providing the electrode assembly in which all of the inner closed curves, if superimposed while preserving orientation and position of the perpendicular cross sections with respect to the cuff, would together define a combined innermost closed curve, and the inner closed curves respectively defined by the perpendicular cross sections enclose respective areas, each of which areas is greater than an area enclosed by the combined innermost closed curve.

For some applications, placing includes placing the electrode assembly around the nerve such that the electrode contacts surfaces are not in physical contact with the nerve.

There is also provided, in accordance with an application of the present invention, a method including:

providing an electrode assembly that includes (1) one or more electrode contact surfaces, and (2) a cuff, to which the electrode contact surfaces are fixed, and which: (a) includes an electrically insulating material, (b) has a longitudinal axis, and (c) is configured to assume open and closed positions, and (d) when in the closed position, is shaped so as to define a plurality of recesses that are recessed radially outwardly from the tubular body tissue, such that the cuff is recessed at every longitudinal location along an entire length of the cuff along the longitudinal axis, and each of the recesses extends along the longitudinal axis of the cuff and has a greatest length, measured in parallel with the longitudinal axis, that is less than 50% of the entire length of the cuff;

while the cuff is in the open position, placing the electrode assembly around tubular body tissue of a subject; and coupling the cuff to the tubular body tissue by causing the cuff to assume the closed position.

For some applications, placing including placing the cuff around a nerve of the subject.

For some applications, coupling includes coupling the cuff to the tubular body tissue such that the cuff comes in contact with the tubular body tissue at a portion of, hut not all, angles with respect to the longitudinal axis, at every longitudinal location along the entire length of the cuff.

For some applications, providing includes providing the electrode assembly in which first and second ones of the recesses overlap each other lengthwise along the cuff, and do not overlap each other anglewise with respect to the longitudinal axis.

For some applications, providing includes providing the electrode assembly in which at least a first one of the inner closed curves extends radially outwardly from the combined innermost volume in a first radial direction, and at least a second one of the inner closed curves, different from the first inner closed curve, extends radially outwardly from the combined innermost volume in a second radial direction different from the first radial direction.

For some applications, placing includes placing the electrode assembly around the nerve such that the electrode contacts surfaces are not in physical contact with the nerve.

There is further provided, in accordance with an application of the present invention, a method including:

providing an electrode assembly that includes (1) one or more electrode contact surfaces, and (2) a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of longitudinal segments, which are (i) distributed continuously along an entire length of the cuff along the longitudinal axis, and (ii) shaped so as to define respective inner closed curves surrounding the longitudinal axis, such that the inner closed curve of each of the segments is of uniform shape along the segment, wherein each of the inner closed curves of at least four of the longitudinal segments has a different shape, and not merely a different size, from the inner closed curve of at least one adjacent longitudinal segment, when orientation and position of the segments with respect to the cuff are preserved, the at least four segments having respective lengths, measured in parallel with the longitudinal axis, each of which is at least 0.1 mm;

while the cuff is in the open position, placing the electrode assembly around tubular body tissue of a subject; and coupling the cuff to the tubular body tissue by causing the cuff to assume the closed position.

For some applications, placing includes placing the electrode assembly around the nerve such that the electrode contacts surfaces are not in physical contact with the nerve.

There is still further provided, in accordance with an application of the present invention, a method including:

providing an electrode assembly that includes (1) one or more electrode contact surfaces, and (2) a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of longitudinal segments, which are (i) distributed continuously along an entire length of the cuff along the longitudinal axis, and (ii) shaped so as to define respective inner closed curves surrounding the longitudinal axis, such that the inner closed curve of each of the segments is of uniform shape along the segment, wherein each of the inner closed curves of at least three of the longitudinal segments has a different shape, and not merely a different size, from the inner closed curve of at least one adjacent longitudinal segment, when orientation and position of the segments with respect to the cuff are preserved, the at least three segments having respective lengths, measured in parallel with the longitudinal axis, each of which is at least 0.1 mm and no more than 50% of the entire length of the cuff;

while the cuff is in the open position, placing the electrode assembly around tubular body tissue of a subject; and coupling the cuff to the tubular body tissue by causing the cuff to assume the closed position.

For some applications, placing includes placing the electrode assembly around the nerve such that the electrode contacts surfaces are not in physical contact with the nerve.

There is additionally provided, in accordance with an application of the present invention, a method including:

providing an electrode assembly that includes (1) a plurality of electrode contact surfaces, and (2) a cuff, to which the electrode contact surfaces are fixed, and which: (a) includes an electrically insulating material, (b) has a longitudinal axis, (c) is configured to assume open and closed positions, and (d) when in the closed position, is shaped so as to define a plurality of longitudinal segments, distributed continuously along an entire length of the cuff along the longitudinal axis, the segments having respective planar cross sections perpendicular to the longitudinal axis, which perpendicular cross sections define respective inner closed curves surrounding the longitudinal axis, such that the inner closed curve of each of the segments is of uniform shape along the segment;

while the cuff is in the open position, placing the electrode assembly around tubular body tissue of a subject; and coupling the cuff to the tubular body tissue by causing the cuff to assume the closed position, such that:
  a first one of the segments is shaped so as to define one or more first recesses that are recessed radially outward from the tubular body tissue,
  a second one of the segments is shaped so as to define one or more second recesses that are recessed radially outward from the tubular body tissue,
  a first one of the electrode contact surfaces is fixed within one of the first recesses, the one of the first recesses being recessed radially outward from the tubular body tissue at a first range of angles with respect to the longitudinal axis,
  a second one of the electrode contact surfaces is fixed within one of the second recesses, the one of the second recesses being recessed radially outward from the tubular body tissue at a second range of angles with respect to the longitudinal axis,
  one or more third ones of the segments longitudinally separate the first segment from the second segment, and each of the respective inner closed curves of the third segments coincides with the combined innermost closed curve at both the first and second ranges of angles with respect to the longitudinal axis, and
  perpendicular cross-sectional areas respectively enclosed by the third segments are each greater than a perpendicular cross-sectional area of the tubular body tissue.

For some applications, placing includes placing the electrode assembly around the nerve such that the electrode contacts surfaces are not in physical contact with the nerve.

The present invention will be more fully understood from the following detailed description of embodiments thereof, taken together with the drawings, in which:

BRIEF DESCRIPTION OF THE DRAWINGS

FIGS. 3 and 4A-D are schematic longitudinal cut-away and perpendicular cross-sectional illustrations of the cuff of FIGS. 1A-C, respectively, in accordance with an application of the present invention;

FIGS. 10A-C are perpendicular cross-sectional illustrations of the cuff of FIGS. 1A-C, in accordance with an application of the present invention.

DETAILED DESCRIPTION OF APPLICATIONS

Figure 1A:
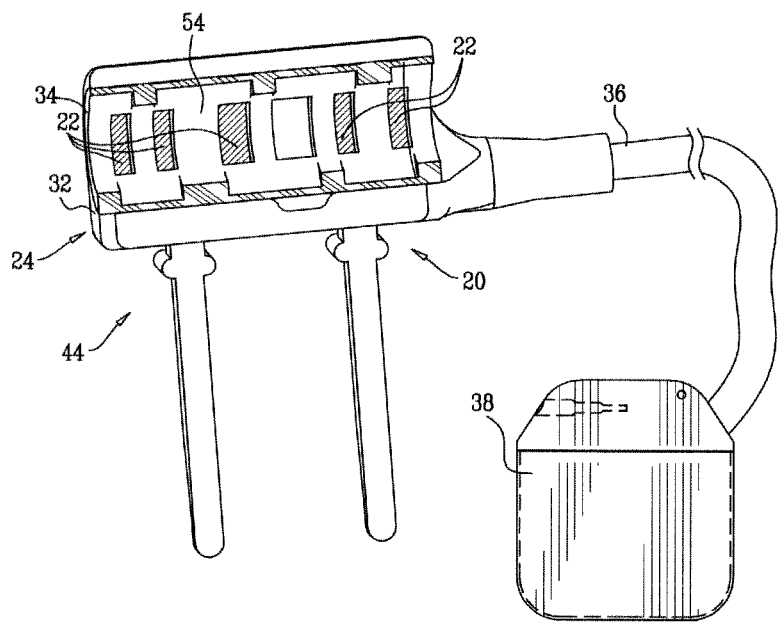
FIG. 1A is a schematic cut-away illustration of an electrode assembly.
Figure 1B:
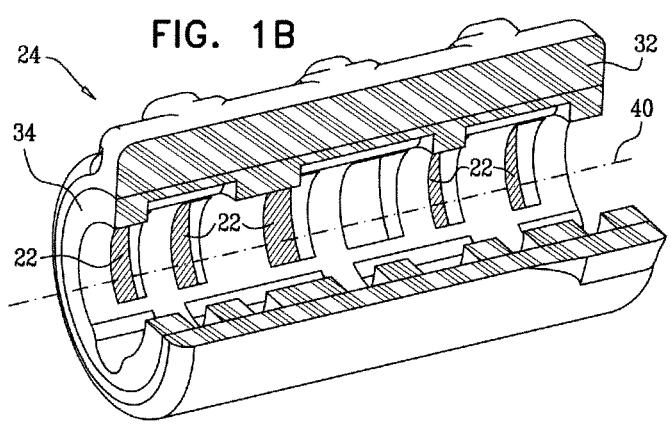
FIGS. 1B and 1C are schematic cut-away illustrations of a cuff of the electrode assembly, in accordance with an embodiment of the present invention.
Figure 1C:
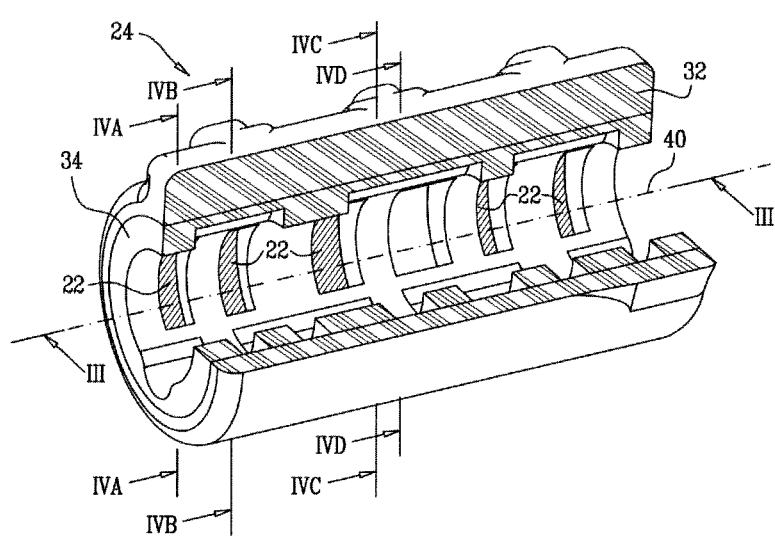

FIG. 1A is a schematic cut-away illustration of an electrode assembly 20, and FIGS. 1B and 1C are schematic cut-away illustrations of a cuff 24 of electrode assembly 20, in accordance with an embodiment of the present invention. Electrode assembly 20 comprises cuff 24 and one or more electrode contact surfaces 22. Cuff 24 is configured to be placed at least partially around (typically entirely around) a nerve or other tubular body tissue, such as a blood vessel, a muscle, a tendon, a ligament, an esophagus, intestine, a fallopian tube, a neck of a gall bladder, a cystic duct, a hepatic duct, a common hepatic duct, a bile duct, and/or a common bile duct. Cuff 24 defines and at least partially surrounds (typically entirely surrounds) a longitudinal axis 40. The cross section of FIG. 1A shows 180 degrees of a circumference of cuff 24 (i.e., 50% of the cuff; the cuff actually completely surrounds 360 degrees of axis 40), while the cross section of FIG. 1B shows 270 degrees of the circumference of the cuff (i.e., 75% of the cuff; the cuff actually completely surrounds 360 degrees of axis 40). Typically, electrode contact surfaces 22 are fixed to cuff 24 such that the contact surfaces are electrically exposed to and face axis 40.

For some applications, as shown in FIGS. 1A-C, cuff 24 comprises an outer housing 32 and an inner insulating tube 34. Outer housing 32 is fixed around inner insulating tube 34, and defines an outer surface of the cuff. Providing these inner and outer layers may facilitate manufacturing of the cuff, including placement of electrode contact surfaces 22 within recesses of the cuff, as described hereinbelow. Housing 32 typically comprises an elastic, electrically-insulating material such as silicone or polyurethane, which may have, for example, a hardness of between about 40 Shore A and about 80 Shore A, such as about 40 Shore A. Inner insulating tube 34 typically comprises an elastic, electrically-insulating material such as silicone or silicone copolymer, which, for some applications, is softer than that of housing 32, for example, having a hardness of between about 1 Shore A and about 40 Shore A, such as about 10 Shore A.

For other applications, cuff 24 comprises a single integrated element, rather than a separate outer housing and inner insulating tube (configuration not shown). The element typically comprises an elastic, electrically-insulating material such as silicone or polyurethane, which may have, for example, a hardness of between about 5 Shore A and about 40 Shore A, such as about 10 Shore A. Alternatively, cuff 24 comprises more than two elements that are fixed to one another.

Electrode assembly 20 optionally further comprises a lead assembly 36, which comprises one or more electrical leads, as is known in the art. The leads are coupled to all or a portion of electrode contact surfaces 22. Lead assembly 36 couples electrode assembly 20 to an implanted or external control unit 38, which comprises appropriate circuitry for driving current between two or more of electrode contact surfaces 22, as is known in the art. Typically, the control unit configures the current such that one or more of the contact surfaces function as cathodes, and one or more function as anodes.

Figure 2A:
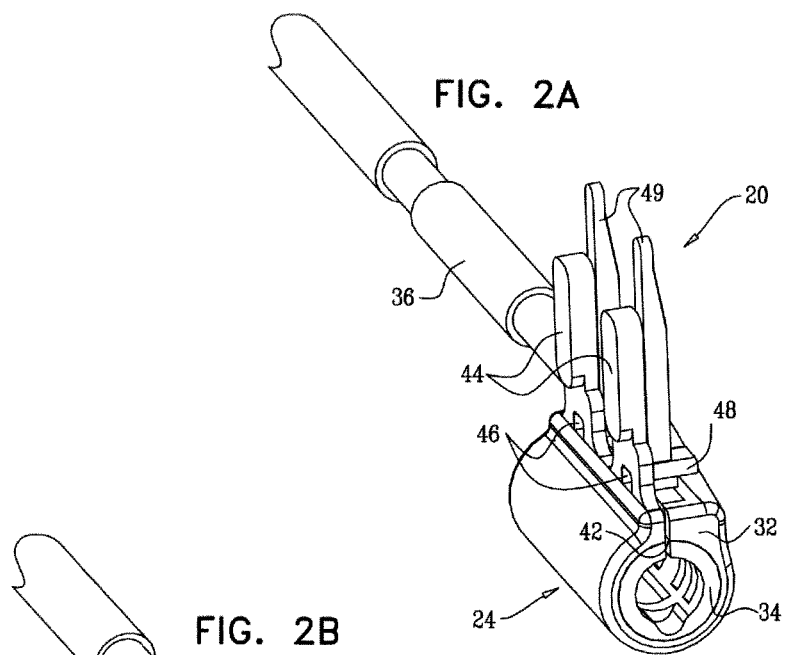
FIGS. 2A and 2B are schematic illustrations of the cuff of FIGS. 1A-C in open and closed positions, respectively, in accordance with an application of the present invention.
Figure 2B:
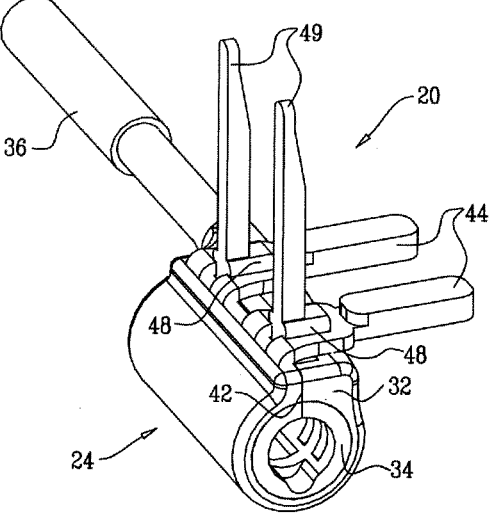

Reference is made to FIGS. 2A and 2B, which are schematic illustrations of cuff 24 in open and closed positions, respectively, in accordance with an application of the present invention. Typically, cuff 24 is shaped so as to define a longitudinal slit 42 along the entire length of the cuff. The cuff assumes the open position when the edges of the slit do not touch each other. The cuff is placed around the tubular body tissue, such as the nerve, by passing the tubular body tissue through the slit. The edges of the slit are brought together to bring the cuff into the closed position.

For some applications, electrode assembly 20 further comprises one or more closing elements 44, which are configured to hold the edges of slit 42 together. For some applications, each of the closing elements comprises an opening 46 near one edge of slit 42 and a corresponding protrusion 48 on the other edge of the slit. To close the cuff, each of the protrusions is inserted into the corresponding slit. Optionally, each of the closing elements further comprises a tab 49, which the surgeon implanting the cuff may grasp to help pull protrusion 48 through opening 46.

Figure 3:
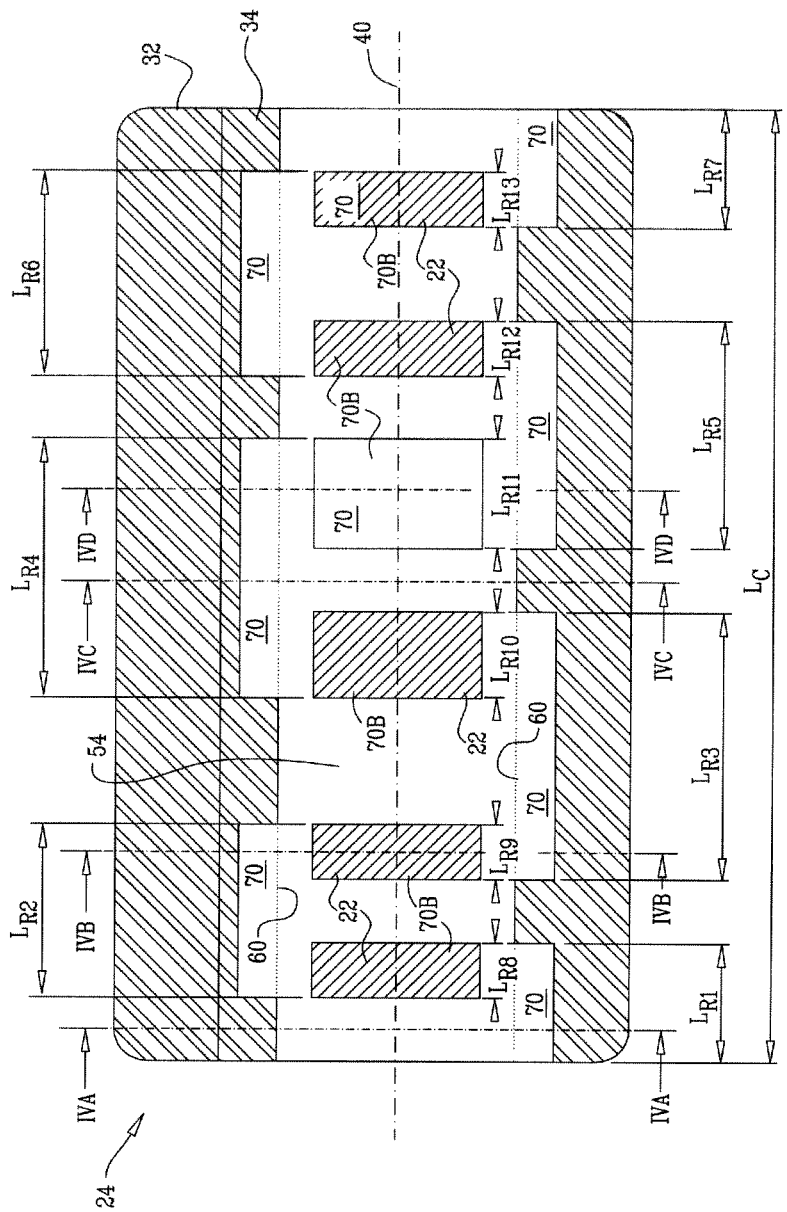

Reference is made to FIGS. 3 and 4A-D, which are schematic longitudinal cut-away and perpendicular cross-sectional illustrations of cuff 24, respectively, in accordance with an application of the present invention. In FIG. 3, the recesses labeled 70B extend in a direction perpendicular to the plane of the page, into the page. When cuff 24 is in the closed position, such as described hereinabove with reference to FIG. 2B, the cuff is shaped so as to define a plurality of planar cross sections perpendicular to longitudinal axis 40, distributed continuously along an entire length $L_C$ of the cuff. Perpendicular cross sections IVA-IVA, IVB-IVB, IVC-IVC, and IVD-IVD, indicated in FIGS. 1C and 3, are three of these perpendicular planar cross sections. The plurality of perpendicular cross sections define respective inner closed curves 52 surrounding longitudinal axis 40. For example, perpendicular cross sections IVA-IVA, IVB-IVB, IVC-IVC, and IVD-IVD, shown in FIGS. 4A, 4B, 4C, and 4D, respectively, define respective inner closed curves 52A, 52B, 52C, and 52D, respectively. Inner closed curves 52 together define an inner surface 54 that defines and completely surrounds a combined innermost volume that extends along entire length $L_C$ of the cuff. Because not all of the inner closed curves have the same shape, the perpendicular cross-sectional shape of volume 56 varies along the length of the cuff. In addition, inner closed curves 52 define and enclose respective inner cross-sectional regions 56.

Entire length $L_C$ of cuff 24, measured along longitudinal axis 40, is typically at least 1 mm, no more than 40 mm, and/or between 1 and 40 mm. Typically, the combined innermost volume has a volume of at least 10 mm3, no more than 5000 mm3, and/or between 10 and 5000 mm3, such as at least 15 mm3, no more than 200 mm3, and/or between 15 and 200 mm3.

Figure 5A:
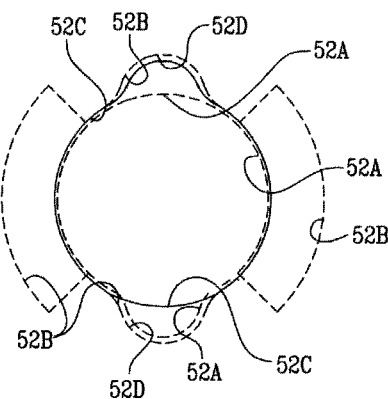
FIGS. 5A and 5B are symbolic perpendicular cross-sectional illustrations of the superimposition of inner closed curves of the cuff of FIGS. 1A-C, in accordance with an application of the present invention.
Figure 5B:
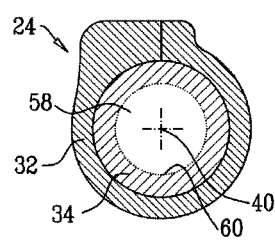

Reference is made to FIGS. 5A and 5B, which are symbolic perpendicular cross-sectional illustrations of the superimposition of inner closed curves 52 of cuff 24, in accordance with an application of the present invention. FIG. 5B additionally shows outer housing 32 and inner insulating tube 34. All of inner closed curves 52, if superimposed while preserving orientation and position of the perpendicular cross sections and the inner closed curves with respect to the cuff, would together define a combined innermost closed curve 60 surrounding longitudinal axis 40. For example, FIG. 5A shows inner curves 52A, 52B, 52C, and 52D superimposed while preserving orientation and position of the perpendicular cross sections and the inner closed curves with respect to cuff 24. (In order to better illustrate the curves, coinciding portions are shown slightly offset from one another, even though they actually coincide.) Curves 52A, 52B, 52C, and 52D, if thus superimposed, would together define a combined innermost closed curve 60 surrounding longitudinal axis 40, as shown in FIG. 5B. (In this example, combined innermost closed curve 60 is a complete circle.) In addition, an intersection of cross-sectional regions 56 (shown, by way of example, in FIGS. 4A-D), if the cross-sectional regions were to be superimposed while preserving orientation and position of the cross-sectional regions with respect to cuff 24, would define a combined inner cross-sectional region 58 (shown, by way of example, in FIG. 5B). Combined inner cross-sectional region 58, if extended along the entire length of cuff 24, would define the combined innermost volume. In addition, a periphery of combined inner cross-sectional region 58 defines combined innermost closed curve 60.

Typically, combined innermost closed curve 60 and/or the combined inner cross-sectional region is shaped to correspond to and/or accommodate the shape of the tubular body tissue, such as the nerve, around which cuff 24 is placed. For some applications, combined innermost closed curve 60 and/or the combined inner cross-sectional region is elliptical, such as circular (as shown in the figures). For other applications, the combined innermost closed curve and/or the combined inner cross-sectional region has another non-elliptical shape, such as a shape chosen to correspond to the anatomical perpendicular cross section of the tubular body tissue, e.g., the nerve, to which the cuff is applied. Combined innermost closed curve 60, if extended along the entire length of cuff 24, would define a combined innermost volume (combined inner cross-sectional region 58, if extended along the entire length of cuff 24, would also define the combined innermost volume). For example, for applications in which combined innermost closed curve 60 is elliptical, the combined innermost volume is an elliptical cylinder, and, for applications in which combined innermost closed curve 60 is elliptical, the combined innermost volume is a circular cylinder. (As used herein, including in the claims, the term "elliptical" includes, but is not limited to, "circular" within its scope.) For some applications in which the combined innermost volume is an elliptical (e.g., circular) cylinder, the cylinder has a major axis that is at least m, no more than 8 mm, and/or between 1 and 8 mm and a minor axis that is at least 0.5 mm, no more than 6 mm, and/or between 0.5 and 6

Generally, the cuff is placeable around an elliptical (e.g., circular) cylinder. The cuff is also placeable around tubular body tissue, such as a nerve, which is not perfectly elliptical, but may be generally elliptical. It is to be understood that the cylinder and the tubular body tissue are not elements of apparatus of the present invention, and are described, and recited in a portion of the claims, for purposes of helping to define the structure of the actual elements of the apparatus. The cylinder may be considered an abstraction of the tubular body tissue, which may be helpful, in some cases, for defining with definiteness the structure of the cuff without reference to parts of the human body.

Cuff 24 is shaped so as to define a plurality of recesses 70 that extend and are recessed radially outwardly from the combined innermost volume. (The recesses also extend radially outwardly from the tubular body tissue if the cuff is placed therearound, and/or from the elliptical cylinder, if the cuff is placed therearound.) At any given angle around longitudinal axis 40 in any given planar cross section perpendicular to axis 40 that includes a recess, the surface of the recess facing longitudinal axis 40 is further from the axis than is the combined innermost closed curve at given the angle and cross section. The recesses extend along the longitudinal axis of the cuff. (In FIGS. 3 and 8, the recesses labeled 70B extend in a direction perpendicular to the plane of the page, into the page.)

For some applications, cuff 24 is shaped such that every one of the planar cross sections perpendicular to axis 40 along entire length $L_C$ of the cuff partially defines at least one of recesses 70, such that cuff 24 is recessed at every longitudinal location along the entire length $L_C$ of the cuff, and at least one of the recesses is at every longitudinal location along the entire length $L_C$ of the cuff. (Any given perpendicular planar cross section only partially, rather than fully, defines at least one of the recesses, because the cross section defines the at least one of the recesses in combination with other cross sections.) In other words, at every longitudinal location along its entire length L, cuff 24 is recessed in at least one radially outward direction (the radially outward directions typically differ at least some of the longitudinal locations). As a result, inner closed curves 52 respectively defined by the perpendicular cross sections enclose respective areas, each of which areas is greater than an area enclosed by combined innermost closed curve 60. It is noted that, for these applications, cuff 24 is recessed even at its longitudinal ends. In other words, even at its ends, cuff 24 is not shaped so as to define an inner surface that coincides with combined innermost closed curve 60. For applications in which cuff 24 is applied to a nerve, recesses 70 may serve to prevent damage to the nerve by allowing the nerve to swell in at least one radial direction into at least one of the recesses, along entire length $L_C$ of the cuff.

For some applications, such as shown in FIGS. 4A and 4C, at least one segment of the cuff is shaped so as to define a single recess 70. Alternatively or additionally, at least one segment of the cuff is shaped so as to define more than one recess 70, such as at least two recesses 70 (e.g., exactly two recesses 70), at least three recesses 70 (e.g., exactly three recesses 70), or at least four recesses 70 (e.g., exactly four recesses 70, as shown in FIGS. 4B and 4D).

For some applications, each of recesses 70 has a length $L_R$ along the cuff that is less than entire length $L_C$ of the cuff, e.g., less than 50%, 40%, 25%, or 15% of length $L_C$. This design generally prevents migration of the tubular body tissue, such as the nerve, over time into the recesses, away from the center of the cuff, as might occur if any of the recesses extended along the entire length, or even most of the length, of the cuff. Holding the cuff in position around the nerve helps maintain good electrical contact between the electrical contact surfaces and the tubular body tissue, such as the nerve. In addition, the recesses thus do not provide a continuous path for current applied by the electrode contact surfaces to pass through the cuff without entering the tubular body tissue, such as the nerve.

Typically, one or more portions of each of inner closed curves 52 coincides with combined innermost closed curve 60, such that each of the inner closed curves coincides with the combined innermost closed curve at a portion of, but not all, angles with respect to axis 40, such that the cuff comes in contact with the tubular body tissue at a portion of, but not all, angles with respect to axis 40. Such contact of these non-recessed portions may help hold the cuff in position around the tubular body structure, thereby aiding in maintaining good electrical contact between the electrical contact surfaces and the tissue.

For some applications, each of the recesses has a length, measured in parallel with longitudinal axis 40, of at least 0.1 min, no more than 15 mm, and/or between 0.1 and 15 mm. For some applications in which cuff 24 defines two or more longitudinal segments 100, as described hereinbelow with reference to FIG. 8, each of the recesses that longitudinally spans a single segment 100 has a length of at least 0.1 mm, no more than 10 mm, and/or between 0.1 and 10 mm, and/or a length of at least 2% of the entire length of the cuff (e.g., at least 5%), no more than 50% of the entire length (e.g., no more than 20%), and/or between 2% and 50% of the entire length (e.g., between 5% and 20%), while each of the recesses that longitudinally spans more than one segment 100 has a length of at least 0.3 mm, no more than 15 mm, and/or between 0.3 and 15 mm, and/or a length of at least 5% of the entire length of the cuff (e.g., at least 10%), no more than 50% of the entire length (e.g., no more than 40%), and/or between 5% and 50% of the entire length (e.g., between 10% and 40%). For some applications, each of the recesses has a length of at least 0.1 mm, such as at least 0.3 mm. Typically, recesses have a plurality of different respective lengths. For example, the cuff may be shaped so as to define recesses having all or a portion of the following respective ranges of lengths and exemplary lengths:

TABLE 1

|  | Range of lengths | Exemplary length |
| --- | --- | --- |
| $L_{R1}$ | 0.3 mm-15 mm | 1.5 mm |
| $L_{R2}$ | 0.3 mm-15 mm | 2.2 mm |
| $L_{R3}$ | 0.3 mm-15 mm | 3.4 mm |
| $L_{R4}$ | 0.3 mm-15 mm | 3.3 mm |
| $L_{R5}$ | 0.3 mm-15 mm | 2.9 mm |
| $L_{R6}$ | 0.3 mm-15 mm | 2.6 mm |
| $L_{R7}$ | 0.3 mm-10 mm | 1.5 mm |
| $L_{R8}$ | 0.1 mm-10 mm | 0.7 mm |
| $L_{R9}$ | 0.1 mm-10 mm | 0.7 mm |
| $L_{R10}$ | 0.1 mm-10 mm | 1.1 mm |
| $L_{R11}$ | 0.1 mm-10 mm | 1.4 mm |
| $L_{R12}$ | 0.1 mm-10 mm | 0.7 mm |
| $L_{R13}$ | 0.1 mm-10 mm | 0.7 mm |

For some applications, the recesses having these lengths are arranged as shown in FIG. 3. For other applications, the recesses are otherwise arranged.

Typically, at least some of recesses 70 overlap one another lengthwise along the cuff (i.e., along axis 40), either partially or completely, without overlapping anglewise with respect to axis 40 (i.e., the recesses are recessed radially outward from the axis 40 at different, non-overlapping angles with respect to the axis, so that the recesses do not intersect one another). As a result, at least one of the perpendicular cross sections partially defines at least two of the recesses. For example, as shown in FIG. 3, a first recess having length $L_{R1}$ partially overlaps lengthwise a second recess having length $L_{R2}$ (with an overlap length of 0.7 mm). The first recess is recessed in an upward direction in the figure, while the second recess is recessed in a downward direction in the figure, such that the first and second recesses do not overlap each other anglewise with respect to axis 40. The second recess (having length $L_{R2}$) additionally overlaps lengthwise a third recess having length $L_{R3}$ (by 0.7 mm). For some applications, a first one of recesses 70 partially overlaps lengthwise a second one of recesses 70 with an overlap length of at least 0.1 mm, no more than 15 mm, and/or between 0.1 and 15 mm, and/or an overlap length equal to at least 10%, no more than 60%, and/or between 10% and 60% of the length of the first one of the recesses. In addition, for example, as shown in FIG. 3, the recess having length $L_{R2}$ partially overlaps the recesses having lengths $L_{R7}$ and $L_{R8}$ (by the entire lengths of $L_{R7}$ and $L_{R8}$). For some applications, recesses 70 that partially overlap lengthwise each other do not overlap each other anglewise; in other words, the recesses extend in different, non-overlapping radial directions.

Reference is still made to FIGS. 3 and 4A-D. Cuff 24 is typically shaped such that each planar cross section thereof perpendicular to axis 40 includes one or more non-recessed portions 72 that coincide with combined innermost closed curve 60. These non-recessed portions serve in part to hold the cuff in position around the tubular body tissue, such as a nerve.

Reference is made to FIGS. 4A-D. For some applications, at least two of recesses 70 extend radially outwardly in different radial directions, such as in opposite radial directions. For example, the recess shown in FIG. 4A extends radially outwardly in the opposite radial direction of the recess shown in FIG. 4C. For some applications, the at least two of the recesses that extend radially outwardly in different radial directions are defined at least in part by a common perpendicular cross section. For example, perpendicular cross section IVB-IVB, shown in FIG. 4B, defines a first recess that extends upward in the figure, and a second recess that extends downward in the figure, i.e., in opposite radial directions.

Reference is again made to FIGS. 4A, 4C, and 5B. For some applications, at least two of the perpendicular cross sections of cuff 24 define respective inner closed curves 52 that have different shapes, and not merely different sizes, when orientation and position of the perpendicular cross sections and inner closed curves with respect to the cuff are preserved. For example, assume that a first perpendicular cross section has the circular shape of combined innermost closed curve 60, shown in FIG. 5B, and a second perpendicular cross section has the shape of inner closed curve 52A, shown in FIG. 4A. These two perpendicular cross sections have different shapes. Likewise, two perpendicular cross sections having the shapes of inner closed curves 52A and 52C, shown in FIGS. 4A and 4C, respectively, would also have different shapes, when orientation and position of the perpendicular cross sections and inner closed curves with respect to the cuff are preserved (even though inner closed curves 52A and 52C would have the same shape if orientation were not preserved). However, two circular perpendicular cross sections having different radii would not have different shapes, but merely different sizes.

As used in the present application, including in the claims, "preserving orientation" of the perpendicular cross sections and/or inner closed curves with respect to the cuff means not rotating the perpendicular cross sections or and inner closed curves, such as not rotating the perpendicular cross sections or inner closed curves around longitudinal axis 40. For example, inner closed curves 52A and 52C, shown in FIGS. 4A and 4C, respectively, are considered to have different shapes when preserving orientation of the perpendicular cross sections and inner closed curves with respect to the cuff. This is the case even though inner closed curves 52A and 52C would have the same shape if one of the inner closed curves were to be rotated 180 degrees around longitudinal axis 40, i.e., if the orientation of the inner closed curves with the cuff were not preserved. As used in the present application, including in the claims, "preserving position" of the perpendicular cross sections and/or inner closed curves with respect to the cuff means not translating the perpendicular cross sections and/or inner closed curves within their respective planes, e.g., changing offsets of the perpendicular cross sections and/or inner closed curves with respect to longitudinal axis 40. For example, assume that two inner closed curves were both circles of the same size. These two circular inner closed curves would be considered to have the same shape, even though they would cross each other if one of the inner closed curves were translated in any direction in its plane.

Figure 6:
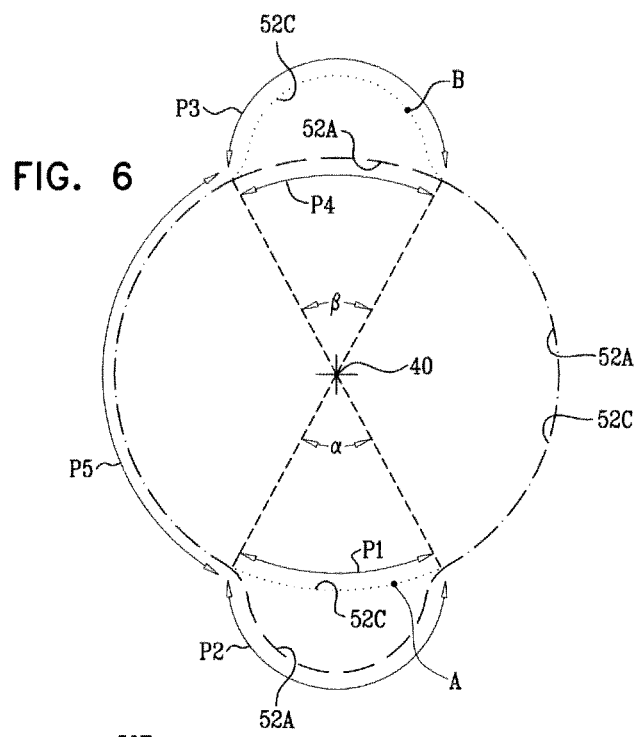
FIG. 6 is a schematic illustration of the crossing and intersection of two of the inner closed curves of FIGS. 4A-D, in accordance with an application of the present invention.

Reference is now made to FIG. 6, which is a schematic illustration of the crossing and intersection of two of the inner closed curves of FIGS. 4A-D, in accordance with an application of the present invention. In this application, inner closed curves 52 of the at least two of the perpendicular cross sections would cross, and not merely intersect, one another if superimposed while preserving orientation and position of the perpendicular cross sections and inner closed curves with respect to the cuff. For example, in FIG. 6 inner closed curve 52A (of FIG. 4A) and inner closed curve 52C (of FIG. 4C) are shown superimposed. As can be seen, inner closed curves 52A and 52C cross each other, and do not merely intersect. For example, a portion P1 of inner closed curve 52C is closer to longitudinal axis 40 of the combined perpendicular cross section than is a portion P2 of inner closed curve 52A at the same first range of angles α from axis 40, while a portion P3 of inner closed curve 52C is further from axis 40 than is a portion P4 of inner closed curve 52A at the same second range of angles β from axis 40. This is only possible because the inner closed curves cross each other. In other words, any path along inner closed curve 52C from a point A on portion P1 to a point B on portion P3 must cross inner closed curve 52A, i.e., go from one side of inner closed curve 52A with respect to axis 40 (the inner side) to the other side of inner closed curve 52A with respect to axis 40 (the outer side). It is noted that inner closed curves 52A and 52C cross one another, even though they may coincide (such as along a portion P5) for a certain range of angles with respect to axis 40 while crossing.

Figure 7A:
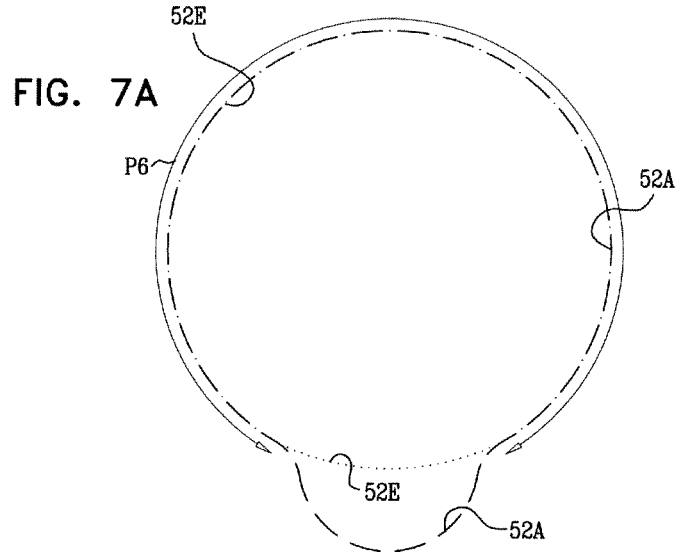
FIGS. 7A and 7B are schematic illustrations of the intersection, but not crossing, of two sets of inner closed curves.
Figure 7B:
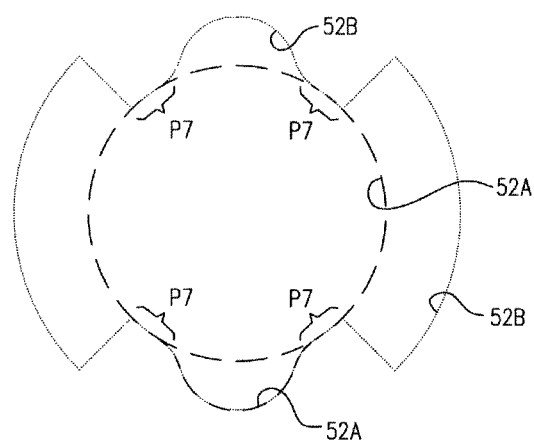

FIGS. 7A and 7B are schematic illustrations of the intersection, but not crossing, of two sets of inner closed curves. In FIG. 7A inner closed curve 52A (of FIG. 4A) (shown as dashed in FIG. 7A) and a circular inner closed curve 52E (shown as dotted) are shown superimposed. As can be seen, inner closed curves 52A and 52E merely intersect (along a portion P6), but do not cross each other. In FIG. 7B inner closed curve 52A (of FIG. 4A) (shown as dashed in FIG. 7B) and inner closed curve 52B (shown as dotted) are shown superimposed. As can be seen, inner closed curves 52A and 52B merely intersect (along portions P7), but do not cross each other.

For some applications, inner closed curve 52 of at least one of the perpendicular cross sections is rotationally non-symmetric for all rotational angles. For example, inner closed curve 52A, shown in FIG. 4A, is rotationally non-symmetric for all rotational angles. Optionally, inner closed curves 52 of at least two of the perpendicular cross sections having different shapes (when orientation and position of the perpendicular cross sections and inner closed curves with respect to the cuff are preserved) are rotationally non-symmetric for all rotational angles. For example, inner closed curves 52A and 52C, shown in FIGS. 4A and 4C, respectively, have different shapes (when orientation and position of the perpendicular cross sections and inner closed curves with respect to the cuff are preserved), and are rotationally non-symmetric for all rotational angles. Optionally, inner closed curves 52 of all of the perpendicular cross sections may be rotationally non-symmetric (configuration not shown). Optionally, for each of these different degrees of rotational non-symmetry, combined innermost closed curve 60, described hereinabove with reference to FIGS. 5A-B, may be circular.

Reference is again made to FIGS. 4A-D. For some applications, such as shown in FIG. 4B, one or more of recesses 70 have respective electrode contact surfaces 22 fixed therein, such that the electrode contact surfaces are recessed radially outward from combined innermost closed curve 60. As a result, when cuff 24 is placed around the tubular body tissue, such as the nerve, the electrode contact surfaces are not in physical contact with the nerve when the cuff is placed around the tissue. In addition, one or more of recesses 70 may not have an electrode contact surface coupled therein, such as shown in FIGS. 1A, 1B, 4A, 4C, and 4D.

Alternatively or additionally, one or more of electrode contact surfaces 22 are coupled to non-recessed portions 72 of cuff 24 that coincide with combined innermost closed curve 60, which are described hereinabove with reference to FIGS. 3 and 4A-D. As a result, when cuff 24 is placed around the tubular body tissue, such as the nerve, the electrode contact surfaces are in physical contact with the tissue.

Figure 8:
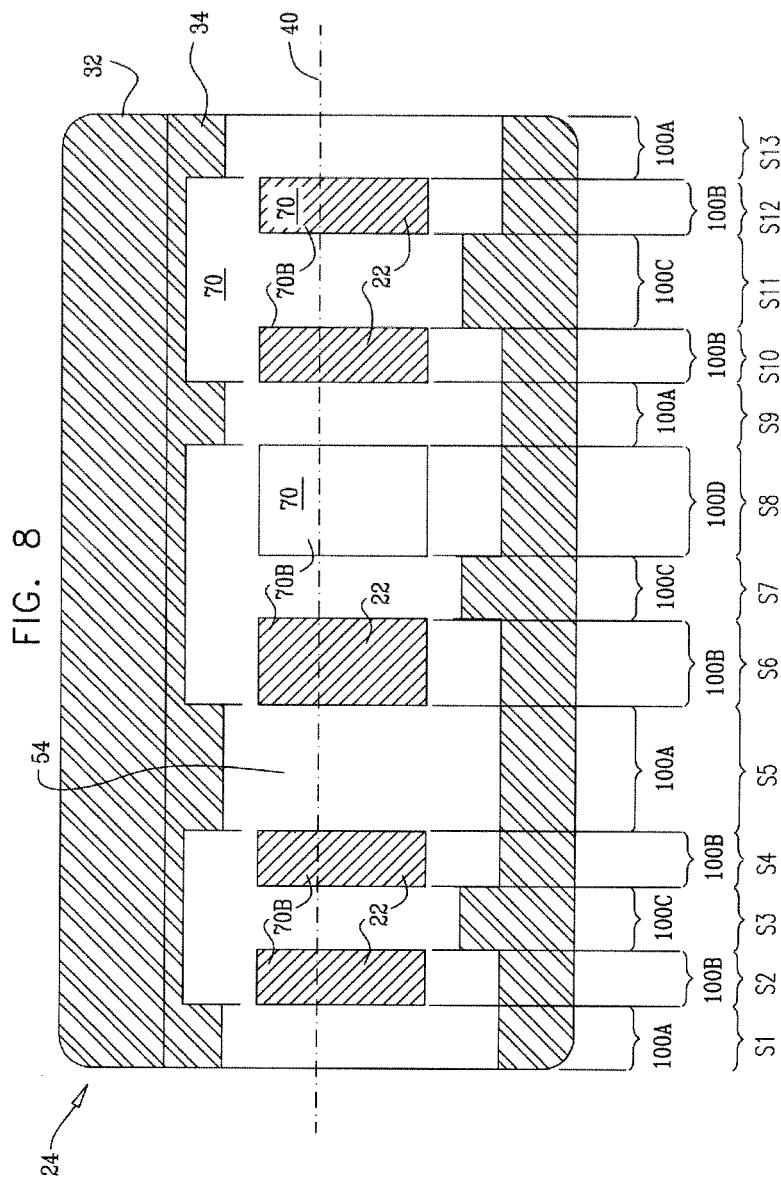
FIG. 8 is a schematic longitudinal cut-away illustration of the cuff of FIGS. 1A-C, in accordance with an application of the present invention.

Reference is made to FIG. 8, which is a schematic longitudinal cut-away illustration of cuff 24, in accordance with an application of the present invention. In FIG. 8, the recesses labeled 70B extend in a direction perpendicular to the plane of the page, into the page. In this application, cuff 24 is constructed so as to define two or more longitudinal segments 100, distributed continuously along the entire length of the cuff. The segments typically do not overlap one another lengthwise along the cuff. The segments are differentiated from one another by their perpendicular cross-sectional shapes and/or by whether they include electrode contact surfaces 22. The segments have respective planar cross sections perpendicular to longitudinal axis 40, which perpendicular cross sections define respective inner closed curves surrounding the longitudinal axis, such that the inner closed curve of a given segment 100 is of uniform shape along the entire given segment, when orientation and position of the perpendicular cross sections and inner closed curves with respect to the cuff are preserved. For some applications, the inner closed curve of each of at least a portion, e.g., all, of the segments is of uniform site along the segment. Alternatively or additionally, the inner closed curve of each of at least a portion, e.g., all, of the segments is of non-uniform size along the segment (for example, the size of inner closed curve may monotonically increase along the segment).

For some applications, inner curves of at least three (such as at least four, at least five, at least ten, or all) longitudinally-adjacent segments 100 have different shapes, and not merely different sizes, when orientation and position of the segments with respect to the cuff are preserved. For some applications, the segments have respective lengths, measured in parallel with longitudinal axis 40, each of which is at least 0.1 mm (e.g., at least 0.5 mm), no more than 50% of the entire length of the cuff (e.g., no more than 20%), and/or between 0.1 mm (e.g., 0.5 mm) and 50% of the entire length of the cuff (e.g., 20%). For some applications, two of segments 100 that include respective electrode contact surfaces 22 are separated by at least one of segments 100 that does not include any electrode contact surfaces.

During manufacture, inner insulating tube 34 of cuff 24 is typically molded as a single piece that is shaped so as to define the segments. The segments are typically not made as separate pieces and subsequently affixed to one another.

For some applications, cuff 24 defines at least three segments 100, such as at least four, at least five, at least six, at least 10, at least 13, or at least 15 segments 100. For some applications, at least two of segments 100 that are not longitudinally adjacent to each other have the same shape, when orientation and position of the segments with respect to the cuff are preserved. For example, segments 100 may have a total of two, three, four, or five different shapes, such that a portion of the segments share a common one of these shapes.

For some applications, segments 100 include segments types 100A, 100B, 100C, and 100D, some of which repeat along the cuff more than once. Each of these instances of a segment type has the same shape (when orientation and position of the segments with respect to the cuff are preserved) as the other instances of the segment type, but may have a different length (along axis 40 of the cuff) from the other instances of the segment type. For some applications, the recess defined by a first segment type (e.g., segment type 100A) extends radially outward beyond innermost closed curve 60 generally in a first radial direction (e.g., downward in FIG. 8), while the recess defined by a second segment type (e.g., segment type 100C) extends radially outward beyond innermost closed curve 60 generally in a second radial direction different from the first radial direction (e.g., upward in FIG. 8), such as generally opposite to the first radial direction, e.g., between 120 and 180 degrees from the first radial direction, such as 180 degrees from the first radial direction.

For some applications, first and second ones of segment types 100 have the same shape (when orientation and position of the segments with respect to the cuff are preserved), but differ in that the first segment type (e.g., segment type 100B) includes one of electrode contact surfaces 22, while the second segment type (e.g., segment type 100D) does not include any of electrode contact surfaces 22.

Typically, each of segments 100A, 100B, 100C, and 100D has a longitudinal length along the cuff of at least 0.2 mm, such as at least 0.5 mm. For some applications, the length of each segment is at least 0.2 mm, no more than 20 mm, and/or between 0.2 and 20 mm, such as at least 0.5 mm, no more than 4 mm, and/or between 0.5 and 4 mm.

For some applications, segment types 100A, 100B, 100C, and 100D have the shapes of perpendicular cross sections IVA-IVA, IVB-IVB, IVC-IVC, and IVD-IVD, respectively, indicated in FIGS. 1C and 3, and shown in FIGS. 4A-D.

In one particular configuration of cuff 24 illustrated in FIG. 8, segments 100 comprise 13 segments S1-S13. For example, the segments may have the segment types (shapes) and ranges of lengths or exemplary lengths shown in the following table:

TABLE 2

| Segment | Segment type | Range of lengths | Exemplary length |
| --- | --- | --- | --- |
| S1 | 100A | 0.1 mm-10 mm | 0.8 mm |
| S2 | 100B | 0.1 mm-10 mm | 0.7 mm |
| S3 | 100C | 0.1 mm-10 mm | 0.8 mm |
| S4 | 100B | 0.1 mm-10 mm | 0.7 mm |
| S5 | 100A | 0.1 mm-10 mm | 1.6 mm |
| S6 | 100B | 0.1 mm-10 mm | 1.1 mm |
| S7 | 100C | 0.1 mm-10 mm | 0.8 mm |
| S8 | 100D | 0.1 mm-10 mm | 1.4 mm |
| S9 | 100A | 0.1 mm-10 mm | 0.8 mm |
| S10 | 100B | 0.1 mm-10 mm | 0.7 mm |
| S11 | 100C | 0.1 mm-10 mm | 1.2 mm |
| S12 | 100B | 0.1 mm-10 mm | 0.7 mm |
| S13 | 100A | 0.1 mm-10 mm | 0.8 mm |

Thus, for example, segments S1 and S5 have the same perpendicular cross-sectional shape as each other (when orientation and position of the segments with respect to the cuff are preserved), but may have different lengths from each other. For some applications, a recess 70 defined by a first segment type (e.g., segment type 100A) extends generally in a first radial direction, while a recess 70 defined by a second segment type (e.g., segment type 100C) extends generally in a second radial direction different from the first radial direction, such as generally opposite to the first radial direction, e.g., between 120 and 180 degrees from the first radial direction, such as 180 degrees from the first radial direction.

As mentioned above, for some applications, a portion of segments 100 include electrode contact surfaces 22, in one or more of the recesses defined by the segment. The following tables set forth two exemplary distributions of the electrode contact surfaces in the segments. The tables also indicate, by way of example, which of the surfaces are configured by control unit 38 (FIG. 1A) to function as cathode(s), which as anode(s), and which as passive electrode(s). Each of the passive electrodes is coupled to at least one other passive electrode, and is electrically device-coupled to neither (a) any circuitry that is electrically device-coupled to at least one cathode or at least one anode, nor (b) an energy source. The passive electrodes may be implemented using techniques described in U.S. Pat. No. 7,627,384 to Ayal et al., which is incorporated herein by reference.

TABLE 3

| Segment | Electrode type |
| --- | --- |
| S2 | Passive electrode |
| S4 | Anode |
| S6 | Cathode |
| S10 | Cathode |
| S12 | Passive electrode |

TABLE 4

| Segment | Electrode type |
| --- | --- |
| S2 | Passive electrode |
| S4 | Cathode |
| S6 | Anode |
| S10 | Anode |
| S12 | Passive electrode |

For some applications, segment S8 does not include an electrode contact surface. For some applications, each of the segments that includes an electrode contact surface includes two or more electrode contact surfaces, fixed within respective recesses of the segment that extend in different radial directions. For example, the segments containing electrode contact surfaces may have cross sections shaped as shown in FIG. 4B, and may contain exactly two electrode contact surfaces 22 in respective recesses 70 that extend in opposite direction (e.g., in FIG. 4B, to the right and to the left).

For some applications, segment types 100A, 100B, 100C, and 100D of Table 2 have the shapes of perpendicular cross sections IVA-IVA, IVB-IVB, IVC-IVC, and IVD-IVD, respectively, indicated in FIGS. 1C and 3, and shown in FIGS. 4A-D.

Figure 9:
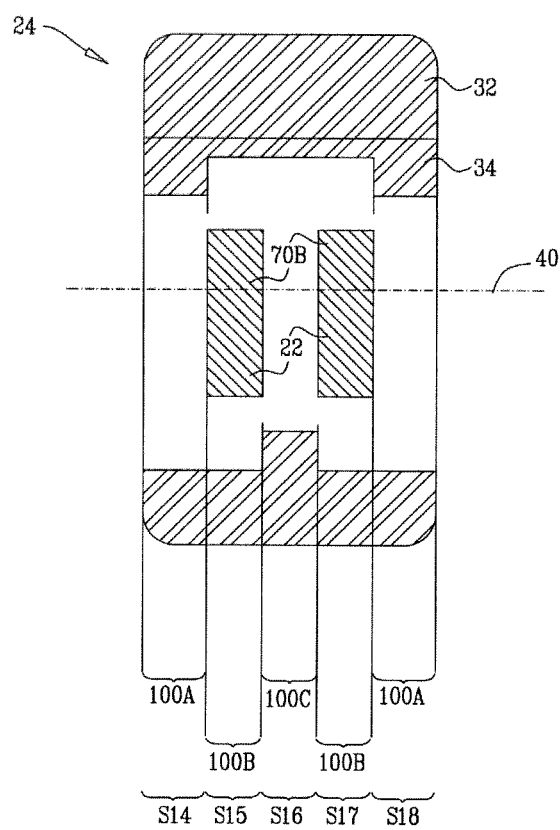
FIG. 9 is a schematic longitudinal cut-away illustration of an alternative configuration of the cuff of FIGS. 1A-C, in accordance with an application of the present invention.

Reference is made to FIG. 9, which is a schematic longitudinal cut-away illustration of an alternative configuration of cuff 24, in accordance with an application of the present invention. In FIG. 9, the recesses labeled 70B extend in a direction perpendicular to the plane of the page, into the page. In this particular configuration, cuff 24 is constructed so as to define five longitudinal segments 100, distributed continuously along the entire length of the cuff. Two of the longitudinal segments include respective electrode contact surfaces 22. The segments are differentiated from one another by their perpendicular cross-sectional shapes and/or by whether they include electrode contact surfaces 22. The segments have respective planar cross sections perpendicular to longitudinal axis 40, which perpendicular cross sections define respective inner closed curves surrounding the longitudinal axis, such that the inner closed curve of a given segment 100 is of uniform shape and size along the entire given segment, when orientation and position of the perpendicular cross sections and inner closed curves with respect to the cuff are preserved. For some applications, inner curves of longitudinally-adjacent segments 100 have different shapes, and not merely different sizes, when orientation and position of the segments with respect to the cuff are preserved. The two of segments 100 that include respective electrode contact surfaces 22 are separated by at least one of segments 100 that does not include any electrode contact surfaces.

During manufacture, inner insulating tube 34 of cuff 24 is typically molded as a single piece that is shaped so as to define the segments. The segments are typically not made as separate pieces and subsequently affixed to one another.

In the particular configuration shown in FIG. 9, cuff 24 defines five segments 100, which include segment types 100A, 100B, and 100C, some of which repeat along the cuff more than once. Each of these instances of a segment type has the same shape (when orientation and position of the segments with respect to the cuff are preserved) as the other instances of the segment type, but may have a different length (along axis 40 of the cuff) from the other instances of the segment type. For some applications, the recess defined by a first segment type (e.g., segment type 100A) extends radially outward beyond innermost closed curve 60 generally in a first radial direction (e.g. downward in FIG. 9), while the recess defined by a second segment type (e.g., segment type 100C) extends radially outward beyond innermost closed curve 60 generally in a second radial direction different from the first radial direction (e.g., upward in FIG. 9), such as generally opposite to the first radial direction, e.g., between 120 and 180 degrees from the first radial direction, such as 180 degrees from the first radial direction.

Typically, each of segments 100A, 100B, and 100C has a longitudinal length along the cuff of at least 0.2 mm, such as at least 0.5 mm. For some applications, the length of each segment is at least 0.2 mm, no more than 20 mm, and/or between 0.2 and 20 mm, such as at least 0.5 mm, no more than 4 mm, and/or between 0.5 and 4 mm. For some applications, segment types 100A, 100B, and 100C have the shapes of perpendicular cross sections IVA-IVA, IVB-IVB, and IVC-IVC, respectively, indicated in FIGS. 1C and 3, and shown in FIGS. 4A-C.

In the particular configuration of cuff 24 illustrated in FIG. 9, segments 100 comprise five segments S14-S18. For example, the segments may have the segment types (shapes) and ranges of lengths or exemplary lengths shown in the following table:

TABLE 5

| Segment | Segment type | Range of lengths | Exemplary length |
| --- | --- | --- | --- |
| S14 | 100A | 0.1 mm-10 mm | 0.8 mm |
| S15 | 100B | 0.1 mm-10 mm | 0.7 mm |
| S16 | 100C | 0.1 mm-10 mm | 0.8 mm |
| S17 | 100B | 0.1 mm-10 mm | 0.7 mm |
| S18 | 100A | 0.1 mm-10 mm | 1.6 mm |

Thus, for example, segments S14 and S18 have the same perpendicular cross-sectional shape as each other (when orientation and position of the segments with respect to the cuff are preserved), but may have different lengths from each other. For some applications, a recess 70 defined by a first segment type (e.g., segment type 100A) extends generally in a first radial direction, while a recess 70 defined by a second segment type (e.g., segment type 100C) extends generally in a second radial direction different from the first radial direction, such as generally opposite to the first radial direction, e.g., between 120 and 180 degrees from the first radial direction, such as 180 degrees from the first radial direction.

As mentioned above, in this particular configuration, two of segments 100 include electrode contact surfaces 22, in one or more of the recesses defined by the segment. The following tables set forth two exemplary distributions of the electrode contact surfaces in the segments. The tables also indicate, by way of example, which of the surfaces are configured by control unit 38 (FIG. 1A) to function as a cathode, and which as an anode.

TABLE 6

| Segment | Electrode type |
| --- | --- |
| S15 | Cathode |
| S17 | Anode |

TABLE 7

| Segment | Electrode type |
| --- | --- |
| S15 | Anode |
| S17 | Cathode |

For some applications, each of the segments that includes an electrode contact surface includes two or more electrode contact surfaces, fixed within respective recesses of the segment that extend in different radial directions. For example, the segments containing electrode contact surfaces may have cross sections shaped as shown in FIG. 4B, and may contain exactly two electrode contact surfaces 22 in respective recesses 70 that extend in opposite direction (e.g., in FIG. 4B, to the right and to the left).

For some applications, segment types 100A, 100B, and 100C of Table 5 have the shapes of perpendicular cross sections IVA-IVA, IVB-IVB, and IVC-IVC, respectively, indicated in FIGS. 1C and 3, and shown in FIGS. 4A-C.

Reference is made to FIGS. 10A-C, which are perpendicular cross-sectional illustrations of the cuff of FIGS. 1A-C, in accordance with an application of the present invention. For some applications, cuff 24 is configured to include at least first and second segments 100 that include respective first and second electrode contact surfaces 22, fixed within first and second recesses 70, respectively (each of the segments may further include additional electrode surfaces in other respective recesses defined by the segment, and/or additional recesses without electrode surfaces). The first and second segments are longitudinally separated by one or more third segments 100, which typically do not include electrode contact surfaces. The first, second, and third segments are configured such that the one or more third segments electrically isolates the first electrode contact surface from the second electrode contact surface when cuff 24 is placed around the tubular body tissue, such as the nerve. As a result, current driven by control unit 38 (FIG. 1A) between the first and second electrode contact surfaces passes substantially through the tubular body tissue, rather than through the at least a third segment, or between an inner surface of the third segment and the tubular body tissue. In other words, all conductive paths between the first and second electrode contact surfaces pass through the tubular body tissue, and not between the tubular body tissue and the inner surface of the at least a third segment.

For some applications, the first recess is recessed radially outward from the combined innermost volume at a first range of angles with respect to axis 40, and the second recess is recessed radially outward from the combined innermost volume at a second range of angles with respect to axis 40. Typically, the first and second ranges of angles coincide. For example, the first and second segments may both have the cross-sectional shape shown in FIG. 10B, and the first and second ranges of angles may extend from about 45 degrees to 135 degrees, as indicated by an angle α (alpha) in FIG. 10B (assuming that 0 degrees is upwards in the figure). The one or more third segments (which longitudinally separate the first segment from the second segment) have respective inner closed curves 52 that coincide with combined innermost closed curve 60 at both the first and second range of angles.

For example, one or more of the third segments may have the cross-sectional shape shown in FIG. 10A, such that inner closed curve 52A coincides with innermost closed curve 60 at the range of angles indicated by angle α (alpha) in FIG. 10A (about 45 degrees to about 135 degrees).

In an alternative example, the third segments may include two segments, one of which has the cross-sectional shape shown in FIG. 10A, and the other the cross-sectional shape shown in FIG. 10C, in which inner closed curve 52C coincides with innermost closed curve 60 at the range of angles indicated by angle α (alpha) in FIG. 10C (about 45 degrees to about 135 degrees).

Alternatively or additionally, for some applications, cuff 24 surrounds a volume (which corresponds generally to the tubular body tissue for applications in which the cuff is applied to the tubular body tissue) that is defined by extending combined innermost closed curve 60 (described hereinabove with reference to FIGS. 5A-B) along the entire length of the cuff. Any current driven by the control unit between the first and second electrode contact surfaces must pass through this volume, rather than through the at least a third segment, or between an inner surface of the third segment and the volume. In other words, all conductive paths between the first and second electrode contact surfaces pass through the volume, and not between the volume and the inner surfaces of the at least a third segment.

Typically, the perpendicular cross-sectional area enclosed by the at least a third segment is greater than the perpendicular cross-sectional area of the tubular body tissue and/or volume surrounded by the at least a third segment. The at least a third segment nevertheless provides electrical isolation between the first and second segments, because the at least a third segment comes in physical contact with the tubular body tissue and/or volume in the radial direction(s) of electrode contact surfaces. One or more recesses 70 defined by the at least a third segment are recessed in one or more radial directions different from the one or more directions of electrode contact surfaces 22.

For example, as shown in FIG. 8, the first and second segments may be of segment type 100B (e.g., segments S2 and S4), and the at least a third segment may be of segment type 100C (e.g., segment S3). Segment types 100B and 100C may correspond to the perpendicular cross sections shown in FIGS. 4B and 4C, respectively. Segment S3, having the shape of FIG. 4C, includes insulating material on its right and left sides in FIG. 4C, which isolates electrode contact surfaces 22 of segments S2 and S4 from each other. Recess 70 of segment S3, because it is recessed in another direction (upward in FIG. 4C), does not prevent this electrical isolation.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Provisional Patent Application 60/383,157 to Ayal et al., filed May 23, 2002, entitled. "Inverse recruitment for autonomic nerve systems,"

International Patent Application PCT/IL02/00068 to Cohen et al., filed Jan. 23, 2002, entitled, "Treatment of disorders by unidirectional nerve stimulation," and U.S. patent application Ser. No. 10/488,334, in the national stage thereof, which published as US Patent Application Publication 2004/0243182, U.S. patent application Ser. No. 09/944,913 to Cohen and Gross, filed Aug. 31, 2001, entitled. "Treatment of disorders by unidirectional nerve stimulation," which issued as U.S. Pat. No. 6,684,105, U.S. patent application Ser. No. 09/824,682 to Cohen and Ayal, filed Apr. 4, 2001, entitled "Method and apparatus for selective control of nerve fibers," which issued as U.S. Pat. No. 6,600,954, U.S. patent application Ser. No. 10/205,475 to Gross et al., filed Jul. 24, 2002, entitled, "Selective nerve fiber stimulation for treating heart conditions," which published as US Patent Application Publication 2003/0045909, U.S. patent application Ser. No. 10/205,474 to Gross et al., filed Jul. 24, 2002, entitled, "Electrode assembly for nerve control," which issued as U.S. Pat. No. 6.907.295, International Patent Application PCT/IL03/00431 to Ayal et al., filed May 23, 2003, entitled, "Selective nerve fiber stimulation for treating heart conditions," which published as PCT Publication WO 03/099377 to Ayal et al., International Patent Application PCT/IL03/00430 to Ayal et al., filed May 23, 2003, entitled. "Electrode assembly for nerve control," which published as PCT Publication WO 03/099373 to Ayal et al. and U.S. patent application Ser. No. 10/529,149, in the national stage thereof, which published as US Patent Application Publication 2006/0116739, U.S. patent application Ser. No. 10/719,659 to Ben David et al., filed Nov. 20, 2003, entitled, "Selective nerve fiber stimulation for treating heart conditions," which published as US Patent Application Publication 2004/0193231, U.S. patent application Ser. No. 11/022,011 to Cohen et al., filed Dec. 22, 2004, entitled, "Construction of electrode assembly for nerve control," which issued as U.S. Pat. No. 7,561,922, U.S. patent application Ser. No. 11/234,877 to Ben-David et al., filed Sep. 22, 2005, entitled, "Selective nerve fiber stimulation," which published as US Patent Application Publication 2006/0100668, U.S. patent application Ser. No. 11/280,884 to Ayal et al., filed Nov. 15, 2005, entitled, "Techniques for nerve stimulation," which issued as U.S. Pat. No. 7,627,384, U.S. patent application Ser. No. 11/517,888 to Ben-Ezra et al., filed Sep. 7, 2006, entitled, "Techniques for reducing pain associated with nerve stimulation," which published as US Patent Application Publication 2008/0065158, U.S. patent application Ser. No. 12/217,930 to Ben-David et al., filed Jul. 9, 2008, entitled, "Electrode cuffs," which published as US Patent Application Publication 2010/0010603, U.S. patent application Ser. No. 11/347,120, filed Feb. 2, 2006, which published as US Patent Application Publication 2006/0195170, U.S. patent application Ser. No. 12/228,630 to Ben-David et al., filed Aug. 13, 2008, entitled, "Electrode devices for nerve stimulation and cardiac sensing," which published as US Patent Application Publication 2010/0042186, and/or U.S. patent application Ser. No. 12/947,608, filed Nov. 16, 2010.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an electrode assembly, which comprises:
   one or more electrode contact surfaces; and
   a cuff, to which the electrode contact surfaces are fixed, and which: (a) comprises an electrically insulating material, (b) has a longitudinal axis, (c) is configured to assume open and closed positions, and (d) when in the closed position, is shaped so as to define:
      (i) a plurality of planar cross sections perpendicular to the longitudinal axis, distributed continuously along an entire length of the cuff along the longitudinal axis, such that the perpendicular cross sections define respective inner closed curves surrounding the longitudinal axis, which inner closed curves define and enclose respective inner cross-sectional regions, wherein an intersection of the cross-sectional regions, if the cross-sectional regions were to be superimposed while preserving orientation and position of the cross-sectional regions with respect to the cuff, would define a combined inner cross-sectional region, which, if extended along the entire length of the cuff, would define a combined innermost volume, and
      (ii) a plurality of recesses that are recessed radially outwardly from the combined innermost volume, each of which recesses extends along the longitudinal axis of the cuff and has a greatest length, measured in parallel with the longitudinal axis, that is less than 50% of the entire length of the cuff,
   wherein the inner closed curves enclose respective areas, each of which areas is greater than an area of the combined inner cross-sectional region.

2. The apparatus according to claim 1, wherein the entire length of the cuff is between 1 and 40 mm.

3. The apparatus according to claim 1, wherein the cuff is shaped such that the combined inner cross-sectional region is circular.

4. The apparatus according to claim 1, wherein a periphery of the combined inner cross-sectional region defines a combined innermost closed curve, and wherein each of the inner closed curves coincides with the combined innermost closed curve at a portion of, but not all, angles with respect to the longitudinal axis.

5. The apparatus according to claim 1, wherein first and second ones of the recesses overlap each other lengthwise along the cuff, and do not overlap each other anglewise with respect to the longitudinal axis.

6. The apparatus according to claim 1, wherein at least a first one of the inner closed curves extends radially outwardly from the combined innermost volume in a first radial direction, and wherein at least a second one of the inner closed curves, different from the first inner closed curve, extends radially outwardly from the combined innermost volume in a second radial direction different from the first radial direction.

7. The apparatus according to claim 1, wherein the cuff is configured to assume the open and closed positions by defining a slit therethrough that extends along the entire length of the cuff.

8. The apparatus according to claim 1,
   wherein 13 sets of pluralities of the perpendicular cross sections define 13 segments of the cuff, respectively, such that the perpendicular cross sections are contiguous within each of the sets, and the sets are arranged in numerical order from a first set to a thirteenth set along the cuff, such that none of the segments overlap one other lengthwise along the cuff,
   wherein the 13 segments have respective first through thirteenth lengths, measured in parallel with the longitudinal axis, each of which is at least 0.1 mm,
   wherein the inner closed curves of the first, fifth, ninth, and thirteenth segments have the same shape as one another, while preserving orientation and position of the inner closed curves with respect to the cuff,
   wherein the inner closed curves of the second, fourth, sixth, tenth, and twelfth segments have the same shape as one another, while preserving orientation and position of the inner closed curves with respect to the cuff,
   wherein the inner closed curves of the third, seventh, and eleventh segments have the same shape as one another, while preserving orientation and position of the inner closed curves with respect to the cuff,
   wherein the inner closed curve of the eighth segment has a shape that is different from the shapes of the inner closed curves of the other segments, while preserving orientation and position of the inner closed curves with respect to the cuff,
   wherein respective ones of the electrode contact surfaces are fixed within the recesses defined by the second, fourth, sixth, tenth, and twelfth segments, and
   wherein none of the electrode contact surfaces is fixed within the recesses defined by the first, third, fifth, seventh, eighth, ninth, eleventh, and thirteenth segments.

9. The apparatus according to claim 8, wherein the first, fifth, ninth, and thirteenth segments define respective ones of the recesses that extend generally in a first radial direction, and wherein the third, seventh, and eleventh segments define respective ones of the recesses that extend generally in a second radial direction different from the first radial direction.

10. The apparatus according to claim 8, wherein the first through thirteenth lengths are 0.8 mm, 0.7 mm, 0.8 mm, 0.7 mm, 1.6 mm, 1.1 mm, 0.8 mm, 1.4 mm, 0.8 mm, 0.7 mm, 1.2 mm, 0.7 mm, and 0.8 mm, respectively.

11. The apparatus according to claim 1,
   wherein 13 sets of pluralities of the perpendicular cross sections define 13 segments of the cuff, respectively, such that the perpendicular cross sections are contiguous within each of the sets, and the sets are arranged in numerical order from a first set to a thirteenth set along the cuff, such that none of the segments overlap one other lengthwise along the cuff,
   wherein the 13 segments have respective first through thirteenth lengths, measured in parallel with the longitudinal axis, each of which is at least 0.1 mm,
   wherein respective ones of the electrode contact surfaces are fixed within the recesses defined of the second, fourth, sixth, tenth, and twelfth segments, wherein none of the electrode contact surfaces is fixed within the recesses defined by the first, third, fifth, seventh, eighth, ninth, eleventh, and thirteenth segments, wherein the apparatus further comprises a control unit, which configures the electrode contact surface fixed in the recess of the fourth segment to function as an anode, and the electrode contact surfaces fixed within the recesses of the sixth and tenth segments to function as cathodes, and wherein the electrode contact surfaces fixed within the recesses of the second and twelfth segments are electrically device-coupled to each other, and are electrically device-coupled to neither the control unit nor an energy source.

12. The apparatus according to claim 1, wherein 13 sets of pluralities of the perpendicular cross sections define 13 segments of the cuff, respectively, such that the perpendicular cross sections are contiguous within each of the sets, and the sets are arranged in numerical order from a first set to a thirteenth set along the cuff, such that none of the segments overlap one other lengthwise along the cuff, wherein the 13 segments have respective first through thirteenth lengths, measured in parallel with the longitudinal axis, each of which is at least 0.1 mm, wherein respective ones of the electrode contact surfaces are fixed within the recesses defined of the second, fourth, sixth, tenth, and twelfth segments, wherein none of the electrode contact surfaces is fixed within the recesses defined by the first, third, fifth, seventh, eighth, ninth, eleventh, and thirteenth segments, wherein the apparatus further comprises a control unit, which configures the electrode contact surface fixed in the recess of the fourth segment to function as an cathode, and the electrode contact surfaces fixed within the recesses of the sixth and tenth segments to function as anodes, and wherein the electrode contact surfaces fixed within the recesses of the second and twelfth segments are electrically device-coupled to each other, and are electrically device-coupled to neither the control unit nor an energy source.

13. The apparatus according to claim 1, wherein at least one of the electrode contact surfaces is fixed within one of the recesses.

14. Apparatus placeable around tubular body tissue, the apparatus comprising an electrode assembly, which comprises:
   one or more electrode contact surfaces; and
   a cuff, to which the electrode contact surfaces are fixed, and which: (a) comprises an electrically insulating material, (b) has a longitudinal axis, (c) is configured to assume open and closed positions, and (d) when in the closed position, is shaped so as to define a plurality of recesses that are recessed radially outwardly from the tubular body tissue if the cuff is placed therearound, such that the cuff is recessed at every longitudinal location along an entire length of the cuff along the longitudinal axis, and each of the recesses extends along the longitudinal axis of the cuff and has a greatest length, measured in parallel with the longitudinal axis, that is less than 50% of the entire length of the cuff.

15. The apparatus according to claim 14, wherein the entire length of the cuff is between 1 and 40 mm.

16. The apparatus according to claim 14, wherein the cuff is shaped so as to come in contact with the tubular body tissue at a portion of, but not all, angles with respect to the longitudinal axis, at every longitudinal location along the entire length of the cuff, if the cuff is placed around the tubular body tissue in the closed position.

17. The apparatus according to claim 14, wherein the tubular body tissue is a nerve, and wherein the cuff is configured to be applied to the nerve.

18. The apparatus according to claim 14, wherein at least one of the electrode contact surfaces is fixed within one of the recesses.

19. Apparatus placeable around an elliptical cylinder having a major axis that is between 1 and 8 mm and a minor axis that is between 0.5 and 6 mm, the apparatus comprising an electrode assembly, which comprises:
   one or more electrode contact surfaces; and
   a cuff, to which the electrode contact surfaces are fixed, and which: (a) comprises an electrically insulating material, (b) has a longitudinal axis, (c) is configured to assume open and closed positions, and (d) when in the closed position, is shaped so as to define a plurality of recesses that are recessed radially outwardly from the cylinder if the cuff is placed therearound, such that the cuff is recessed at every longitudinal location along an entire length of the cuff along the longitudinal axis, and each of the recesses extends along the longitudinal axis of the cuff and has a greatest length, measured in parallel with the longitudinal axis, that is less than 50% of the entire length of the cuff.

20. The apparatus according to claim 19, wherein the cuff is shaped so as to come in contact with the cylinder at a portion of, but not all, angles with respect to the longitudinal axis, at every longitudinal location along the entire length of the cuff, if the cuff is placed around the cylinder in the closed position.

21. The apparatus according to claim 19, wherein at least one of the electrode contact surfaces is fixed within one of the recesses.

22. A method comprising:
   providing an electrode assembly that includes (1) one or more electrode contact surfaces, and (2) a cuff, to which the electrode contact surfaces are fixed, and which: (a) includes an electrically insulating material, (b) has a longitudinal axis, and (c) is configured to assume open and closed positions, and (d) when in the closed position, is shaped so as to define a plurality of recesses that are recessed radially outwardly from the tubular body tissue, such that the cuff is recessed at every longitudinal location along an entire length of the cuff along the longitudinal axis, and each of the recesses extends along the longitudinal axis of the cuff and has a greatest length, measured in parallel with the longitudinal axis, that is less than 50% of the entire length of the cuff;
   while the cuff is in the open position, placing the electrode assembly around tubular body tissue of a subject; and
   coupling the cuff to the tubular body tissue by causing the cuff to assume the closed position.

23. The method according to claim 22, wherein placing comprising placing the cuff around a nerve of the subject.

24. The method according to claim 22, wherein coupling comprises coupling the cuff to the tubular body tissue such that the cuff comes in contact with the tubular body tissue at a portion of, but not all, angles with respect to the longitudinal axis, at every longitudinal location along the entire length of the cuff.

25. The method according to claim 22, wherein providing comprises providing the electrode assembly in which first and second ones of the recesses overlap each other lengthwise along the cuff, and do not overlap each other anglewise with respect to the longitudinal axis.

26. The method according to claim 22, wherein providing comprises providing the electrode assembly in which at least a first one of the inner closed curves extends radially outwardly from the combined innermost volume in a first radial direction, and at least a second one of the inner closed curves, different from the first inner closed curve, extends radially outwardly from the combined innermost volume in a second radial direction different from the first radial direction.

27. The method according to claim 22, wherein placing comprises placing the electrode assembly around the nerve such that the electrode contacts surfaces are not in physical contact with the nerve.

* * * * *